US012685595B2

(12) United States Patent
Sowards et al.

(10) Patent No.: US 12,685,595 B2
(45) Date of Patent: Jul. 21, 2026

(54) CONDUCTOR INCORPORATED FIBER ENABLED MEDICAL SYSTEMS

(71) Applicant: Bard Access Systems, Inc., Salt Lake City, UT (US)

(72) Inventors: Steffan Sowards, Salt Lake City, UT (US); Anthony K. Misener, Bountiful, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 823 days.

(21) Appl. No.: 17/731,129

(22) Filed: Apr. 27, 2022

(65) Prior Publication Data

US 2023/0346482 A1      Nov. 2, 2023

(51) Int. Cl.
A61B 5/00        (2006.01)
A61B 5/01        (2006.01)
(Continued)

(52) U.S. Cl.
CPC ................ A61B 34/20 (2016.02); A61B 5/01 (2013.01); A61B 5/02158 (2013.01);
(Continued)

(58) Field of Classification Search
CPC ... A61B 7/023; A61B 1/00009; A61B 1/0005; A61B 1/00055; A61B 5/037;
(Continued)

(56) References Cited

U.S. PATENT DOCUMENTS 3,493,288 A    2/1970  Oltman et al.
4,768,855 A    9/1988  Nishi et al.
           (Continued)

FOREIGN PATENT DOCUMENTS

CA          3025240  A1   11/2017
DE      102016109601  A1   11/2017
           (Continued)

OTHER PUBLICATIONS

PCT/US2023/015536 filed Mar. 17, 2023 International Preliminary Report on Patentability dated Sep. 10, 2024.
           (Continued)

*Primary Examiner* — May A Abouelela
(74) *Attorney, Agent, or Firm* — Rutan & Tucker LLP

(57)        ABSTRACT

Embodiments disclosed herein are directed to a fiber-optically enabled medical device system including an optical fiber and one or more conductive elements. The optical fiber is configured to determine a shape of the medical device as the device negotiates tortuous vascular pathways. The one or more conductive elements can be configured to transmit electrical signals there along between the distal tip and a console coupled to a proximal end of the medical device. The electrical signals can determine a location of a tip of the medical device, detect an electrophysiological signal at a distal tip, and/or provide electro-stimulation or ablation energy to the distal tip of the medical device. The one or more conductive elements can be a wire extending linearly or helically about the optical fiber, or can be a tube, or tube section, extending annularly about the optical fiber, or combinations thereof.

8 Claims, 11 Drawing Sheets

(51) Int. Cl.

| | |
|---|---|
| *A61B 5/0215* | (2006.01) |
| *A61B 5/0538* | (2021.01) |
| *A61B 5/1455* | (2006.01) |
| *A61B 5/1459* | (2006.01) |
| *A61B 5/367* | (2021.01) |
| *A61B 18/14* | (2006.01) |
| *A61B 34/20* | (2016.01) |
| *A61N 1/05* | (2006.01) |

(52) U.S. Cl.
CPC ........ *A61B 5/0538* (2013.01); *A61B 5/14551* (2013.01); *A61B 5/1459* (2013.01); *A61B 5/367* (2021.01); *A61B 5/6852* (2013.01); *A61B 18/1492* (2013.01); *A61N 1/05* (2013.01); *A61B 2034/2061* (2016.02); *A61B 2562/0266* (2013.01)

(58) Field of Classification Search
CPC ... A61B 7/008; A61B 1/2733; A61B 1/00006; A61B 1/000095; A61B 1/00097; A61B 5/4233; A61B 5/4255; A61B 5/7425; A61B 5/743; A61B 2505/05; A61B 2562/0204; A61B 2562/0247; A61B 2576/02; A61B 1/015; A61B 1/045; A61B 10/00; A61M 13/003; A61M 16/0461; G06T 7/0016; G06T 7/20; G06T 11/00; G06T 2207/10068; G06T 2207/30092; G06T 2210/41; G06T 7/0012
See application file for complete search history.

(56) References Cited

U.S. PATENT DOCUMENTS

| | | | |
|---|---|---|---|
| 4,777,955 A | 10/1988 | Brayton et al. | |
| 4,813,429 A | 3/1989 | Eshel et al. | |
| 4,898,176 A | 2/1990 | Petre | |
| 4,984,581 A | 1/1991 | Stice | |
| 5,099,845 A | 3/1992 | Besz et al. | |
| 5,163,935 A | 11/1992 | Black et al. | |
| 5,178,153 A | 1/1993 | Einzig | |
| 5,207,672 A | 5/1993 | Roth et al. | |
| 5,211,165 A | 5/1993 | Dumoulin et al. | |
| 5,220,703 A | 6/1993 | Kanayama et al. | |
| 5,275,151 A | 1/1994 | Shockey et al. | |
| 5,295,212 A | 3/1994 | Morton et al. | |
| 5,423,321 A | 6/1995 | Fontenot | |
| 5,454,807 A | 10/1995 | Lennox et al. | |
| 5,517,997 A | 5/1996 | Fontenot | |
| 5,599,492 A | 2/1997 | Engelson | |
| 5,622,170 A | 4/1997 | Schulz | |
| 5,633,494 A | 5/1997 | Danisch | |
| 5,693,043 A | 12/1997 | Kittrell et al. | |
| 5,740,808 A | 4/1998 | Panescu et al. | |
| 5,827,313 A | 10/1998 | Ream | |
| 5,872,879 A | 2/1999 | Hamm | |
| 5,873,842 A | 2/1999 | Brennen et al. | |
| 5,879,306 A | 2/1999 | Fontenot et al. | |
| 5,906,579 A | 5/1999 | Vander Salm et al. | |
| 5,957,831 A | 9/1999 | Adair | |
| 6,035,229 A * | 3/2000 | Silverstein | A61B 5/4233 |
| | | | 600/117 |
| 6,069,698 A | 5/2000 | Ozawa et al. | |
| 6,081,741 A | 6/2000 | Hollis | |
| 6,178,346 B1 | 1/2001 | Amundson et al. | |
| 6,208,887 B1 | 3/2001 | Clarke | |
| 6,210,362 B1 | 4/2001 | Ponzi | |
| 6,258,118 B1 | 7/2001 | Baum et al. | |
| 6,319,227 B1 | 11/2001 | Mansouri-Ruiz | |
| 6,343,227 B1 | 1/2002 | Crowley | |
| 6,371,928 B1 | 4/2002 | Mcfann et al. | |
| 6,398,721 B1 | 6/2002 | Nakamura et al. | |
| 6,485,482 B1 | 11/2002 | Belef | |
| 6,563,105 B2 * | 5/2003 | Seibel | H04N 23/55 |
| | | | 250/234 |
| 6,564,089 B2 | 5/2003 | Izatt et al. | |
| 6,593,884 B1 | 7/2003 | Gilboa et al. | |
| 6,597,941 B2 | 7/2003 | Fontenot et al. | |
| 6,619,857 B2 | 9/2003 | Miyake | |
| 6,650,923 B1 | 11/2003 | Lesh et al. | |
| 6,685,666 B1 | 2/2004 | Fontenot | |
| 6,687,010 B1 | 2/2004 | Horii et al. | |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 6,975,803 B2 | 12/2005 | Koide et al. | |
| 7,043,287 B1 * | 5/2006 | Khalil | A61B 5/1455 |
| | | | 600/316 |
| 7,132,645 B2 | 11/2006 | Korn | |
| 7,273,056 B2 | 9/2007 | Wilson et al. | |
| 7,344,533 B2 | 3/2008 | Pearson et al. | |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 | 10/2009 | Casscells, III et al. | |
| 7,699,855 B2 | 4/2010 | Anderson et al. | |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 | 8/2011 | Wilson et al. | |
| 8,032,200 B2 | 10/2011 | Tearney et al. | |
| 8,054,469 B2 | 11/2011 | Nakabayashi et al. | |
| 8,060,187 B2 | 11/2011 | Marshik-Geurts et al. | |
| 8,073,517 B1 | 12/2011 | Burchman | |
| 8,078,261 B2 | 12/2011 | Imam | |
| 8,182,433 B2 * | 5/2012 | Leo | A61B 90/96 |
| | | | 600/587 |
| 8,187,189 B2 | 5/2012 | Jung et al. | |
| 8,197,494 B2 | 6/2012 | Jaggi et al. | |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 | 12/2013 | Snow et al. | |
| 8,622,935 B1 * | 1/2014 | Leo | A61B 5/0084 |
| | | | 604/95.01 |
| 8,700,358 B1 | 4/2014 | Parker, Jr. | |
| 8,781,555 B2 | 7/2014 | Burnside et al. | |
| 8,798,721 B2 | 8/2014 | Dib | |
| 8,968,331 B1 | 3/2015 | Sochor | |
| 8,979,871 B2 | 3/2015 | Tyc et al. | |
| 9,119,551 B2 | 9/2015 | Qi et al. | |
| 9,186,046 B2 | 11/2015 | Ramamurthy et al. | |
| 9,339,206 B2 | 5/2016 | Grunwald | |
| 9,339,221 B1 * | 5/2016 | Heaton, II | A61B 5/742 |
| 9,345,510 B2 | 5/2016 | Patel et al. | |
| 9,360,630 B2 | 6/2016 | Jenner et al. | |
| 9,549,685 B2 | 1/2017 | Cox et al. | |
| 9,560,954 B2 | 2/2017 | Jacobs et al. | |
| 9,572,492 B2 | 2/2017 | Simpson et al. | |
| 9,622,706 B2 | 4/2017 | Dick et al. | |
| 9,645,326 B1 | 5/2017 | Sausse et al. | |
| 9,649,048 B2 | 5/2017 | Cox et al. | |
| 9,678,275 B1 | 6/2017 | Griffin | |
| 9,678,284 B2 | 6/2017 | Coggi et al. | |
| 9,737,213 B1 * | 8/2017 | Heaton, II | A61B 1/31 |
| 9,872,978 B1 | 1/2018 | Zaborsky et al. | |
| 10,231,643 B2 | 3/2019 | Grunwald | |
| 10,231,753 B2 | 3/2019 | Burnside et al. | |
| 10,258,240 B1 * | 4/2019 | Eberle | A61B 5/0084 |
| 10,265,133 B1 | 4/2019 | McClellan | |
| 10,327,830 B2 | 6/2019 | Grant et al. | |
| 10,349,890 B2 | 7/2019 | Misener et al. | |
| 10,448,837 B2 | 10/2019 | Manzke et al. | |

(56)  References Cited

U.S. PATENT DOCUMENTS

| | | | |
|---|---|---|---|
| 10,492,876 B2 | 12/2019 | Anastassiou et al. | |
| 10,551,245 B2 * | 2/2020 | Do | A61B 1/0655 |
| 10,568,586 B2 | 2/2020 | Begin et al. | |
| 10,603,126 B2 | 3/2020 | Karguth et al. | |
| 10,620,386 B2 | 4/2020 | Van Der Mark et al. | |
| 10,631,718 B2 | 4/2020 | Petroff et al. | |
| 10,687,891 B2 * | 6/2020 | Belhe | A61B 18/1492 |
| 10,932,670 B2 | 3/2021 | Smith et al. | |
| 10,939,889 B2 | 3/2021 | Flexman et al. | |
| 10,992,078 B2 | 4/2021 | Thompson et al. | |
| 10,992,079 B2 | 4/2021 | Stats et al. | |
| 11,000,207 B2 | 5/2021 | Burnside et al. | |
| 11,000,265 B1 | 5/2021 | Ryu et al. | |
| 11,103,321 B2 | 8/2021 | Braun et al. | |
| 11,123,047 B2 | 9/2021 | Jaffer et al. | |
| 11,259,892 B2 | 3/2022 | Hufford et al. | |
| 11,284,916 B2 | 3/2022 | Patel et al. | |
| 11,369,342 B2 * | 6/2022 | Irisawa | A61B 5/0095 |
| 11,382,653 B2 | 7/2022 | Patel et al. | |
| 11,474,310 B2 | 10/2022 | Sowards et al. | |
| 11,525,670 B2 | 12/2022 | Messerly et al. | |
| 11,547,282 B2 | 1/2023 | Weise et al. | |
| 11,607,150 B2 | 3/2023 | Schweikert et al. | |
| 11,621,518 B2 | 4/2023 | Stats et al. | |
| 11,630,009 B2 | 4/2023 | Misener et al. | |
| 11,707,205 B2 | 7/2023 | Messerly et al. | |
| 11,806,096 B2 | 11/2023 | Flatt et al. | |
| 11,850,073 B2 | 12/2023 | Wright et al. | |
| 11,931,112 B2 | 3/2024 | Thompson et al. | |
| 12,038,338 B2 | 7/2024 | Misener et al. | |
| 12,048,478 B2 * | 7/2024 | Tegg | A61B 18/1477 |
| 12,089,815 B2 | 9/2024 | Sowards et al. | |
| 2002/0019627 A1 | 2/2002 | Maguire et al. | |
| 2002/0087206 A1 | 7/2002 | Hirschberg et al. | |
| 2002/0166190 A1 | 11/2002 | Miyake et al. | |
| 2002/0188285 A1 | 12/2002 | Brown | |
| 2002/0198457 A1 | 12/2002 | Tearney et al. | |
| 2003/0045798 A1 | 3/2003 | Hular et al. | |
| 2003/0092995 A1 | 5/2003 | Thompson | |
| 2004/0039274 A1 * | 2/2004 | Benaron | A61B 5/0075 |
| | | | 600/342 |
| 2004/0111020 A1 | 6/2004 | Long | |
| 2004/0111147 A1 | 6/2004 | Rabkin et al. | |
| 2004/0242995 A1 | 12/2004 | Maschke | |
| 2004/0247268 A1 * | 12/2004 | Ishihara | A61B 5/0084 |
| | | | 385/117 |
| 2004/0260182 A1 | 12/2004 | Zuluaga et al. | |
| 2005/0033264 A1 | 2/2005 | Redinger | |
| 2005/0113719 A1 * | 5/2005 | Saadat | A61B 5/14542 |
| | | | 600/339 |
| 2005/0272975 A1 * | 12/2005 | McWeeney | A61B 1/307 |
| | | | 600/172 |
| 2006/0013523 A1 * | 1/2006 | Childlers | G02B 6/02042 |
| | | | 385/12 |
| 2006/0030753 A1 * | 2/2006 | Boutillette | A61B 1/0052 |
| | | | 600/153 |
| 2006/0036164 A1 | 2/2006 | Wilson et al. | |
| 2006/0069305 A1 * | 3/2006 | Couvillon | A61B 1/00103 |
| | | | 606/1 |
| 2006/0100610 A1 | 5/2006 | Wallace et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0060847 A1 | 3/2007 | Leo et al. | |
| 2007/0156019 A1 | 7/2007 | Larkin et al. | |
| 2007/0179485 A1 | 8/2007 | Yeik et al. | |
| 2007/0201793 A1 | 8/2007 | Askins et al. | |
| 2007/0225563 A1 * | 9/2007 | Ogino | A61B 1/0055 |
| | | | 600/130 |
| 2007/0253673 A1 | 11/2007 | Nielsen et al. | |
| 2007/0265503 A1 | 11/2007 | Schlesinger et al. | |
| 2007/0287886 A1 | 12/2007 | Saadat | |
| 2007/0299425 A1 | 12/2007 | Waner et al. | |
| 2008/0034519 A1 | 2/2008 | Fujiwara | |
| 2008/0172119 A1 | 7/2008 | Yamasaki et al. | |
| 2008/0183128 A1 | 7/2008 | Morriss et al. | |
| 2008/0281293 A1 | 11/2008 | Peh et al. | |
| 2008/0285909 A1 | 11/2008 | Younge et al. | |
| 2009/0005675 A1 | 1/2009 | Grunwald et al. | |
| 2009/0018393 A1 | 1/2009 | Dick et al. | |
| 2009/0046980 A1 | 2/2009 | Rohlen | |
| 2009/0062634 A1 | 3/2009 | Say et al. | |
| 2009/0137952 A1 | 5/2009 | Ramamurthy et al. | |
| 2009/0208143 A1 | 8/2009 | Yoon et al. | |
| 2009/0227992 A1 | 9/2009 | Nir et al. | |
| 2009/0234328 A1 | 9/2009 | Cox et al. | |
| 2009/0253967 A1 | 10/2009 | Gill et al. | |
| 2009/0270729 A1 | 10/2009 | Corbucci et al. | |
| 2009/0304582 A1 | 12/2009 | Rousso et al. | |
| 2009/0318757 A1 | 12/2009 | Singh | |
| 2009/0324161 A1 | 12/2009 | Prisco | |
| 2010/0016729 A1 | 1/2010 | Futrell | |
| 2010/0030063 A1 * | 2/2010 | Lee | A61B 5/06 |
| | | | 600/424 |
| 2010/0063534 A1 | 3/2010 | Kugler et al. | |
| 2010/0114115 A1 | 5/2010 | Schlesinger et al. | |
| 2010/0114190 A1 | 5/2010 | Bendett et al. | |
| 2010/0139669 A1 | 6/2010 | Piferi et al. | |
| 2010/0204569 A1 | 8/2010 | Burnside et al. | |
| 2010/0274235 A1 * | 10/2010 | Mihajlovic | A61B 5/0084 |
| | | | 606/41 |
| 2010/0286531 A1 | 11/2010 | Ryan et al. | |
| 2010/0292758 A1 | 11/2010 | Lee et al. | |
| 2011/0087112 A1 | 4/2011 | Leo et al. | |
| 2011/0098533 A1 | 4/2011 | Onoda et al. | |
| 2011/0144481 A1 | 6/2011 | Feer et al. | |
| 2011/0144630 A1 | 6/2011 | Loeb | |
| 2011/0166442 A1 | 7/2011 | Sarvazyan | |
| 2011/0172680 A1 | 7/2011 | Younge et al. | |
| 2011/0178509 A1 | 7/2011 | Zerfas et al. | |
| 2011/0196248 A1 | 8/2011 | Grunwald | |
| 2011/0245662 A1 | 10/2011 | Eggers et al. | |
| 2011/0295108 A1 | 12/2011 | Cox et al. | |
| 2012/0046562 A1 | 2/2012 | Powers et al. | |
| 2012/0116161 A1 * | 5/2012 | Nieman | A61J 15/0069 |
| | | | 600/156 |
| 2012/0143029 A1 | 6/2012 | Silverstein et al. | |
| 2012/0184827 A1 | 7/2012 | Shwartz et al. | |
| 2012/0184955 A1 | 7/2012 | Pivotto et al. | |
| 2012/0321243 A1 | 12/2012 | Younge et al. | |
| 2013/0096482 A1 | 4/2013 | Bertrand et al. | |
| 2013/0104884 A1 | 5/2013 | Vazales et al. | |
| 2013/0150732 A1 | 6/2013 | Manzke et al. | |
| 2013/0188855 A1 | 7/2013 | Desjardins et al. | |
| 2013/0190741 A1 | 7/2013 | Moll et al. | |
| 2013/0204124 A1 | 8/2013 | Duindam et al. | |
| 2013/0211246 A1 | 8/2013 | Parasher | |
| 2013/0296652 A1 | 11/2013 | Farr | |
| 2013/0296693 A1 | 11/2013 | Wenzel et al. | |
| 2013/0310668 A1 | 11/2013 | Young | |
| 2013/0324840 A1 | 12/2013 | Zhongping et al. | |
| 2014/0031674 A1 | 1/2014 | Newman et al. | |
| 2014/0046261 A1 | 2/2014 | Newman et al. | |
| 2014/0058368 A1 | 2/2014 | Hogue | |
| 2014/0073950 A1 * | 3/2014 | Akui | A61B 1/0002 |
| | | | 600/478 |
| 2014/0088413 A1 | 3/2014 | Von Bucsh et al. | |
| 2014/0121468 A1 | 5/2014 | Eichenholz | |
| 2014/0155948 A1 | 6/2014 | Walsh et al. | |
| 2014/0180087 A1 * | 6/2014 | Millett | A61B 5/02158 |
| | | | 600/437 |
| 2014/0188133 A1 | 7/2014 | Misener | |
| 2014/0221829 A1 | 8/2014 | Maitland et al. | |
| 2014/0259477 A1 | 9/2014 | Huang | |
| 2014/0268167 A1 * | 9/2014 | Friedman | A61B 5/0084 |
| | | | 356/479 |
| 2014/0275997 A1 | 9/2014 | Chopra et al. | |
| 2014/0318825 A1 | 10/2014 | Erb et al. | |
| 2014/0323887 A1 | 10/2014 | Anderson et al. | |
| 2014/0378945 A1 | 12/2014 | Beri | |
| 2015/0029511 A1 | 1/2015 | Hooft et al. | |
| 2015/0031987 A1 | 1/2015 | Pameijer et al. | |

(56)        References Cited

U.S. PATENT DOCUMENTS

| | | |
|---|---|---|
| 2015/0045649 A1 | 2/2015 | O'Dea et al. |
| 2015/0080688 A1 | 3/2015 | Cinbis et al. |
| 2015/0099979 A1 | 4/2015 | Caves et al. |
| 2015/0105654 A1 | 4/2015 | Meyer |
| 2015/0119700 A1 | 4/2015 | Liang et al. |
| 2015/0119724 A1 | 4/2015 | Weber et al. |
| 2015/0209113 A1 | 7/2015 | Burkholz et al. |
| 2015/0209117 A1 | 7/2015 | Flexman et al. |
| 2015/0244465 A1 | 8/2015 | Chou et al. |
| 2015/0270900 A1 | 9/2015 | Hilario et al. |
| 2015/0272445 A1* | 10/2015 | Rozental ............... A61B 8/445 |
| | | 600/407 |
| 2015/0301288 A1 | 10/2015 | Thornton, Jr. |
| 2015/0305816 A1 | 10/2015 | Hadzic |
| 2015/0320977 A1 | 11/2015 | Vitullo et al. |
| 2016/0018602 A1 | 1/2016 | Govari et al. |
| 2016/0151115 A1 | 6/2016 | Karguth et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0256228 A1 | 9/2016 | Haartsen et al. |
| 2016/0262627 A1 | 9/2016 | Hecker et al. |
| 2016/0302762 A1 | 10/2016 | Stigall et al. |
| 2016/0331360 A1 | 11/2016 | Hera et al. |
| 2016/0354038 A1 | 12/2016 | Demirtas et al. |
| 2016/0357007 A1 | 12/2016 | Swanson |
| 2016/0374589 A1 | 12/2016 | Misener et al. |
| 2017/0017048 A1 | 1/2017 | Coggi et al. |
| 2017/0020394 A1 | 1/2017 | Harrington |
| 2017/0052091 A1 | 2/2017 | Mori |
| 2017/0079548 A1 | 3/2017 | Silverstein et al. |
| 2017/0082806 A1 | 3/2017 | Van Der Mark et al. |
| 2017/0196479 A1* | 7/2017 | Liu ...................... A61B 5/6852 |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1* | 9/2017 | Ofek .................. A61M 25/0029 |
| 2017/0290542 A1* | 10/2017 | Chandrasoma ...... A61B 5/4233 |
| 2017/0296037 A1* | 10/2017 | Yoshino ............... A61B 1/0646 |
| 2017/0303824 A1 | 10/2017 | Schlesinger et al. |
| 2017/0311924 A1 | 11/2017 | Sudol |
| 2017/0333136 A1 | 11/2017 | Hladio et al. |
| 2017/0348063 A1 | 12/2017 | Braun et al. |
| 2018/0067268 A1 | 3/2018 | Murakami et al. |
| 2018/0093078 A1* | 4/2018 | Patil ...................... A61B 5/1076 |
| 2018/0095231 A1* | 4/2018 | Lowell ............... H01B 11/1834 |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0175547 A1 | 6/2018 | Hsu |
| 2018/0239124 A1 | 8/2018 | Naruse et al. |
| 2018/0250088 A1 | 9/2018 | Brennan et al. |
| 2018/0264227 A1 | 9/2018 | Flexman et al. |
| 2018/0289243 A1 | 10/2018 | Landey et al. |
| 2018/0289390 A1* | 10/2018 | Amorizzo .............. A61B 34/20 |
| 2018/0289927 A1* | 10/2018 | Messerly .......... A61M 25/0026 |
| 2018/0317751 A1* | 11/2018 | Kuboi ................ A61B 1/00006 |
| 2018/0339134 A1 | 11/2018 | Leo |
| 2018/0360545 A1 | 12/2018 | Cole et al. |
| 2018/0369432 A1 | 12/2018 | Zaborsky |
| 2019/0008376 A1 | 1/2019 | Wortelboer et al. |
| 2019/0059743 A1 | 2/2019 | Ramachandran et al. |
| 2019/0110838 A1 | 4/2019 | Martinez et al. |
| 2019/0110839 A1 | 4/2019 | Rafii-Tari et al. |
| 2019/0110844 A1 | 4/2019 | Misener et al. |
| 2019/0142528 A1 | 5/2019 | Vertikov |
| 2019/0192818 A1* | 6/2019 | Koda ................. A61B 1/00128 |
| 2019/0212761 A1 | 7/2019 | Swanson et al. |
| 2019/0223706 A1 | 7/2019 | Takeuchi et al. |
| 2019/0235182 A1 | 8/2019 | Cheng |
| 2019/0237902 A1 | 8/2019 | Thompson et al. |
| 2019/0271815 A1 | 9/2019 | Van Der Mark et al. |
| 2019/0321110 A1 | 10/2019 | Grunwald et al. |

| | | |
|---|---|---|
| 2019/0343424 A1* | 11/2019 | Blumenkranz ...... A61B 1/0051 |
| 2019/0357875 A1 | 11/2019 | Qi et al. |
| 2019/0374196 A1 | 12/2019 | Courtney et al. |
| 2020/0022587 A1* | 1/2020 | Glover ................. A61B 5/6869 |
| 2020/0046434 A1 | 2/2020 | Graetzel et al. |
| 2020/0060718 A1 | 2/2020 | Patel et al. |
| 2020/0069192 A1* | 3/2020 | Sanborn ................ A61B 5/015 |
| 2020/0093353 A1* | 3/2020 | Tezuka ................... A61B 5/065 |
| 2020/0155073 A1 | 5/2020 | Hwang et al. |
| 2020/0170724 A1 | 6/2020 | Flatt et al. |
| 2020/0188036 A1 | 6/2020 | Ding et al. |
| 2020/0238051 A1* | 7/2020 | Hwang ................ A61B 5/0084 |
| 2020/0261720 A1* | 8/2020 | Danitz ..................... A61N 1/08 |
| 2020/0275827 A1 | 9/2020 | Weise et al. |
| 2020/0305983 A1 | 10/2020 | Yampolsky et al. |
| 2021/0007796 A1 | 1/2021 | Panescu et al. |
| 2021/0030504 A1 | 2/2021 | Thompson et al. |
| 2021/0045814 A1* | 2/2021 | Thompson ............. A61B 34/20 |
| 2021/0113274 A1 | 4/2021 | Bydlon et al. |
| 2021/0154440 A1 | 5/2021 | Misener |
| 2021/0156676 A1 | 5/2021 | Messerly et al. |
| 2021/0205585 A1 | 7/2021 | Ullmann et al. |
| 2021/0215871 A1 | 7/2021 | Hayes et al. |
| 2021/0268229 A1 | 9/2021 | Sowards et al. |
| 2021/0271035 A1 | 9/2021 | Sowards et al. |
| 2021/0275256 A1 | 9/2021 | Sowards et al. |
| 2021/0275257 A1 | 9/2021 | Prior et al. |
| 2021/0278604 A1 | 9/2021 | Rohr Daniel et al. |
| 2021/0282867 A1* | 9/2021 | Tegg ...................... A61B 5/062 |
| 2021/0290315 A1 | 9/2021 | Lampert et al. |
| 2021/0298680 A1 | 9/2021 | Sowards et al. |
| 2021/0299879 A1 | 9/2021 | Pinter et al. |
| 2021/0325172 A1 | 10/2021 | Hendriks et al. |
| 2021/0330398 A1 | 10/2021 | Tegg et al. |
| 2021/0389519 A1 | 12/2021 | Choi et al. |
| 2021/0401456 A1 | 12/2021 | Cox et al. |
| 2021/0401509 A1 | 12/2021 | Misener et al. |
| 2021/0402144 A1* | 12/2021 | Messerly .............. A61M 25/01 |
| 2022/0034733 A1 | 2/2022 | Misener et al. |
| 2022/0039632 A1 | 2/2022 | Polejaev et al. |
| 2022/0039744 A1* | 2/2022 | Koenig ............... A61B 5/0035 |
| 2022/0110695 A1 | 4/2022 | Sowards et al. |
| 2022/0110706 A1 | 4/2022 | Misener et al. |
| 2022/0133401 A1 | 5/2022 | O'Brien et al. |
| 2022/0152349 A1 | 5/2022 | Sowards et al. |
| 2022/0160209 A1 | 5/2022 | Sowards et al. |
| 2022/0188285 A1 | 6/2022 | Ofenloch |
| 2022/0257975 A1 | 8/2022 | Croll et al. |
| 2022/0330891 A1 | 10/2022 | Sowards et al. |
| 2022/0361762 A1* | 11/2022 | Lalancette ......... A61B 5/02158 |
| 2023/0082991 A1 | 3/2023 | Sowards et al. |
| 2023/0149080 A1* | 5/2023 | Wong .................... A61B 34/37 |
| | | 606/33 |
| 2023/0285085 A1 | 9/2023 | Misener et al. |
| 2023/0292997 A1 | 9/2023 | Sowards et al. |
| 2023/0293243 A1 | 9/2023 | Sowards et al. |
| 2023/0320663 A1 | 10/2023 | Misener et al. |
| 2023/0338090 A1 | 10/2023 | Misener et al. |
| 2023/0346314 A1 | 11/2023 | Sowards et al. |
| 2023/0379057 A1 | 11/2023 | Moore |
| 2023/0414293 A1 | 12/2023 | Farley et al. |
| 2023/0417998 A1 | 12/2023 | Misener et al. |
| 2024/0016425 A1 | 1/2024 | Sowards et al. |
| 2024/0094475 A1 | 3/2024 | Misener et al. |
| 2024/0180470 A1 | 6/2024 | Sowards et al. |
| 2024/0215917 A1 | 7/2024 | Sowards et al. |
| 2024/0423456 A1 | 12/2024 | Sowards et al. |
| 2025/0176853 A1 | 6/2025 | Sowards et al. |
| 2025/0186134 A1 | 6/2025 | Sowards et al. |
| 2025/0249208 A1 | 8/2025 | Sowards et al. |
| 2025/0288366 A1 | 9/2025 | Misener et al. |
| 2026/0076763 A1 | 3/2026 | Sowards et al. |

FOREIGN PATENT DOCUMENTS

| | | |
|---|---|---|
| EP | 2240111 A2 | 10/2010 |
| EP | 2385802 B1 | 8/2013 |
| EP | 3266383 A1 | 1/2018 |
| EP | 2809249 B1 | 12/2018 |

(56) References Cited

FOREIGN PATENT DOCUMENTS

| EP | 3545849 A1 | 10/2019 |
|----|-----------|---------|
| EP | 3725252 A1 | 10/2020 |
| WO | 99/64099 A1 | 12/1999 |
| WO | 1999064099 A1 | 12/1999 |
| WO | 2006080076 A1 | 8/2006 |
| WO | 2006122001 A2 | 11/2006 |
| WO | 2009/155325 A2 | 12/2009 |
| WO | 2011141830 A1 | 11/2011 |
| WO | 2011150376 A1 | 12/2011 |
| WO | 2012064769 A2 | 5/2012 |
| WO | 2012135339 A1 | 10/2012 |
| WO | 2013114376 A1 | 8/2013 |
| WO | 2014049555 A1 | 4/2014 |
| WO | 2015055413 A1 | 4/2015 |
| WO | 2015074045 A2 | 5/2015 |
| WO | 2016/061431 A1 | 4/2016 |
| WO | 2016193051 A1 | 12/2016 |
| WO | 2018071490 A1 | 4/2018 |
| WO | 2018/096491 A1 | 5/2018 |
| WO | 2019037071 A1 | 2/2019 |
| WO | 2019/046769 A1 | 3/2019 |
| WO | 2019230713 A1 | 12/2019 |
| WO | 2020/142470 A1 | 7/2020 |
| WO | 2021021408 A1 | 2/2021 |
| WO | 2021030092 A1 | 2/2021 |
| WO | 2021108688 A1 | 6/2021 |
| WO | 2021108697 A1 | 6/2021 |
| WO | 2021144317 A1 | 7/2021 |
| WO | 2021178578 A1 | 9/2021 |
| WO | 2022/031613 A1 | 2/2022 |
| WO | 2022/081586 A1 | 4/2022 |
| WO | 2022/081723 A1 | 4/2022 |
| WO | 2022109045 A1 | 5/2022 |
| WO | 2022115624 A1 | 6/2022 |
| WO | 2022221608 A1 | 10/2022 |
| WO | 2023043947 A1 | 3/2023 |
| WO | 2023172652 A1 | 9/2023 |
| WO | 2023177822 A1 | 9/2023 |
| WO | 2023177889 A1 | 9/2023 |
| WO | 2023200734 A1 | 10/2023 |
| WO | 2023205257 A1 | 10/2023 |
| WO | 2023212096 A1 | 11/2023 |
| WO | 2023212098 A1 | 11/2023 |
| WO | 2023249952 A1 | 12/2023 |
| WO | 2024015464 A1 | 1/2024 |
| WO | 2024123837 A1 | 6/2024 |

OTHER PUBLICATIONS

PCT/US2023/018076 filed Apr. 10, 2023 International Preliminary Report on Patentability dated Oct. 8, 2024.
U.S. Appl. No. 17/187,536, filed Feb. 26, 2021 Advisory Action dated Oct. 9, 2024.
U.S. Appl. No. 17/187,536, filed Feb. 26, 2021 Notice of Allowance dated Oct. 29, 2024.
U.S. Appl. No. 17/191,551, filed Mar. 3, 2021 Non-Final Office Action dated Aug. 16, 2024.
U.S. Appl. No. 17/529,022, filed Nov. 17, 2021 Non-Final Office Action dated Sep. 30, 2024.
U.S. Appl. No. 17/535,406, filed Nov. 24, 2021 Notice of Allowance dated Oct. 23, 2024.
U.S. Appl. No. 17/731,155, filed Apr. 27, 2022 Non-Final Office Action dated Aug. 22, 2024.
U.S. Appl. No. 17/849,447, filed Jun. 24, 2022 Advisory Action dated Oct. 24, 2024.
U.S. Appl. No. 17/849,447, filed Jun. 24, 2022 Final Office Action dated Aug. 8, 2024.
U.S. Appl. No. 18/141,289, filed Apr. 28, 2023 Non-Final Office Action dated Sep. 28, 2024.
U.S. Appl. No. 18/524,620, filed Nov. 30, 2023 Notice of Allowance dated Sep. 12, 2024.
U.S. Appl. No. 17/187,536, filed Feb. 26, 2021 Final Office Action dated Jul. 2, 2024.
U.S. Appl. No. 17/535,406, filed Nov. 24, 2021 Final Office Action dated Aug. 1, 2024.
U.S. Appl. No. 17/689,773, filed Mar. 8, 2022 Final Office Action dated Aug. 1, 2024.
U.S. Appl. No. 17/696,675, filed Mar. 16, 2022 Non-Final Office Action dated Jun. 11, 2024.
U.S. Appl. No. 17/697,895, filed Mar. 17, 2022 Notice of Allowance dated May 8, 2024.
U.S. Appl. No. 17/725,394, filed Apr. 20, 2022 Restriction Requirement dated Jun. 17, 2024.
U.S. Appl. No. 18/524,620, filed Nov. 30, 2023 Non-Final Office Action dated Jun. 18, 2024.
PCT/US2023/019130 filed Apr. 19, 2023 International Preliminary Report on Patentability dated Oct. 8, 2024.
PCT/US2023/020044 filed Apr. 26, 2023 International Preliminary Report on Patentability dated Oct. 29, 2024.
U.S. Appl. No. 17/191,551, filed Mar. 3, 2021 Notice of Allowance dated Nov. 8, 2024.
U.S. Appl. No. 17/529,022, filed Nov. 17, 2021 Notice of Allowance dated Jan. 2, 2025.
U.S. Appl. No. 17/529,022, filed Nov. 17, 2021 Restriction Requirement dated May 2, 2024.
U.S. Appl. No. 17/689,773, filed Mar. 8, 2022 Advisory Action dated Nov. 1, 2024.
U.S. Appl. No. 17/689,773, filed Mar. 8, 2022 Notice of Allowance dated Jan. 15, 2025.
U.S. Appl. No. 17/696,675, filed Mar. 16, 2022 Advisory Action dated Feb. 6, 2025.
U.S. Appl. No. 17/696,675, filed Mar. 16, 2022 Final Office Action dated Dec. 5, 2024.
U.S. Appl. No. 17/725,394, filed Apr. 20, 2022 Final Office Action dated Mar. 27, 2025.
U.S. Appl. No. 17/725,394, filed Apr. 20, 2022 Non-Final Office Action dated Nov. 19, 2024.
U.S. Appl. No. 17/731,155, filed Apr. 27, 2022 Advisory Action dated Apr. 3, 2025.
U.S. Appl. No. 17/731,155, filed Apr. 27, 2022 Final Office Action dated Jan. 24, 2025.
U.S. Appl. No. 17/849,447, filed Jun. 24, 2022 Non-Final Office Action dated Jan. 17, 2025.
U.S. Appl. No. 17/849,447, filed Jun. 24, 2022 Restriction Requirement dated Apr. 15, 2024.
U.S. Appl. No. 17/863,211, filed Jul. 12, 2022 Non-Final Office Action dated Jan. 29, 2025.
U.S. Appl. No. 17/863,211, filed Jul. 12, 2022 Restriction Requirement dated Nov. 15, 2024.
U.S. Appl. No. 17/945,875, filed Sep. 15, 2022 Non-Final Office Action dated Feb. 27, 2025.
U.S. Appl. No. 18/075,280, filed Dec. 5, 2022 Restriction Requirement dated Mar. 28, 2025.
U.S. Appl. No. 18/141,289, filed Apr. 28, 2023 Notice of Allowance dated Jan. 10, 2025.
U.S. Appl. No. 18/607,165, filed Mar. 15, 2024 Non-Final Office Action dated Jan. 15, 2025.
U.S. Appl. No. 18/607,165, filed Mar. 15, 2024 Notice of Allowance dated Apr. 3, 2025.
U.S. Appl. No. 17/217,852, filed Mar. 30, 2021 Non Final Office Action dated Jun. 7, 2023.
U.S. Appl. No. 17/217,852, filed Mar. 30, 2021 Restriction Requirement dated Mar. 21, 2023.
U.S. Appl. No. 17/697,895, filed Mar. 17, 2022 Non Final Office Action dated Jun. 14, 2023.
PCT/US2023/015416 filed Mar. 16, 2023 International Search Report and Written Opinion dated May 26, 2023.
U.S. Appl. No. 17/187,536, filed Feb. 26, 2021 Non-Final Office Action dated May 17, 2023.
PCT/US2022/024934 filed Apr. 14, 2022 International Search Report and Written Opinion dated Jul. 18, 2022.
PCT/US2023/020042 filed Apr. 26, 2023 International Search Report and Written Opinion dated Sep. 26, 2023.
PCT/US2023/027527 filed Jul. 12, 2023 International Search Report and Written Opinion dated Oct. 16, 2023.

(56) References Cited

OTHER PUBLICATIONS

U.S. Appl. No. 17/187,536, filed Feb. 26, 2021 Advisory Action dated Nov. 21, 2023.
U.S. Appl. No. 17/187,536, filed Feb. 26, 2021 Final Office Action dated Sep. 20, 2023.
U.S. Appl. No. 17/187,536, filed Feb. 26, 2021 Non-Final Office Action dated Dec. 15, 2023.
U.S. Appl. No. 17/217,852, filed Mar. 30, 2021 Notice of Allowance dated Nov. 7, 2023.
U.S. Appl. No. 17/535,406, filed Nov. 24, 2021 Restriction Requirement dated Nov. 24, 2023.
PCT/US2021/024969 filed Mar. 30, 2021 International Search Report and Written Opinion dated Jul. 19, 2021.
PCT/US2021/054596 filed Oct. 12, 2021 International Search Report and Written Opinion dated Jan. 26, 2022.
U.S. Appl. No. 17/185,777, filed Feb. 25, 2021 Notice of Allowance dated Jun. 10, 2022.
PCT/US2021 /059755 filed Nov. 17, 2021 International Search Report and Written Opinion dated Apr. 29, 2022.
PCT/US2021/019713 filed Feb. 25, 2021 International Search Report and Written Opinion dated Jul. 6, 2021.
PCT/US2021/020079 filed Feb. 26, 2021 International Search Report and Written Opinion dated Jun. 4, 2021.
PCT/US2021/020732 filed Mar. 3, 2021 International Search Report and Written Opinion dated Jul. 5, 2021.
PCT/US2021/060849 filed Nov. 24, 2021 International Search Report and Written Opinion dated Mar. 9, 2022.
U.S. Appl. No. 17/185,777, filed Feb. 25, 2021 Non-Final Office Action dated Feb. 9, 2022.
PCT/US2022/043698 filed Sep. 15, 2022 International Search Report and Written Opinion dated Dec. 19, 2022.
U.S. Appl. No. 17/967,794, filed Oct. 17, 2022 Notice of Allowance dated Feb. 15, 2023.
Kirill Bronnikov, Alexey Wolf, Sergey Yakushin, Alexandr Dostovalov, Olga Egorova, Sergey Zhuravlev, Sergey Semjonov, Stefan Wabnitz, and Sergey Babin, "Durable shape sensor based on FBG array inscribed in polyimide-coated multicore optical fiber," Opt. Express 27, 38421-38434 (2019). (Year: 2019).
PCT/US2022/043698 filed Sep. 15, 2022 International Preliminary Report on Patentability dated Mar. 5, 2024.
PCT/US2023/082605 filed Dec. 5, 2023 International Search Report and Written Opinion dated Feb. 28, 2024.
U.S. Appl. No. 17/535,406, filed Nov. 24, 2021 Non-Final Office Action dated Feb. 15, 2024.
U.S. Appl. No. 17/689,773, filed Mar. 8, 2022 Non-Final Office Action dated Mar. 19, 2024.
U.S. Appl. No. 17/697,895, filed Mar. 17, 2022 Non-Final Office Action dated Jan. 11, 2024.
U.S. Appl. No. 17/731,155, filed Apr. 27, 2022 Restriction Requirement dated Feb. 28, 2024.
U.S. Appl. No. 17/849,447, filed Jun. 24, 2022 Non-Final Office Action dated Apr. 10, 2024.
PCT/US2023/014849 filed Mar. 8, 2023 International Search Report and Written Opinion dated Jun. 7, 2023.
PCT/US2023/015536 filed Mar. 17, 2023 International Search Report and Written Opinion dated Jun. 22, 2023.
PCT/US2023/018076 filed Apr. 10, 2023 International Search Report and Written Opinion dated Jul. 11, 2023.
PCT/US2023/019130 filed Apr. 19, 2023 International Search Report and Written Opinion dated Jul. 19, 2023.
PCT/US2023/020044 filed Apr. 26, 2023 International Search Report and Written Opinion dated Jul. 19, 2023.
PCT/US2023/025757 filed Jun. 20, 2023 International Search Report and Written Opinion dated Sep. 11, 2023.
U.S. Appl. No. 17/217,852, filed Mar. 30, 2021 Ex Parte Quayle Action dated Sep. 8, 2023.
U.S. Appl. No. 17/499,644, filed Oct. 12, 2021 Notice of Allowance dated Sep. 18, 2023.
U.S. Appl. No. 17/499,644, filed Oct. 12, 2021 Restriction Requirement dated Jul. 11, 2023.
U.S. Appl. No. 17/697,895, filed Mar. 17, 2022 Advisory Action dated Sep. 8, 2023.
U.S. Appl. No. 17/697,895, filed Mar. 17, 2022 Final Office Action dated Aug. 16, 2023.
U.S. Appl. No. 17/696,675, filed Mar. 16, 2022 Notice of Allowance dated Jun. 17, 2025.
U.S. Appl. No. 17/717,919, filed Apr. 11, 2022 Non-Final Office Action dated Jul. 1, 2025.
U.S. Appl. No. 17/717,919, filed Apr. 11, 2022 Restriction Requirement dated Apr. 23, 2025.
U.S. Appl. No. 17/721,333, filed Apr. 14, 2022 Restriction Requirement dated May 6, 2025.
U.S. Appl. No. 17/725,394, filed Apr. 20, 2022 Advisory Action dated Jun. 5, 2025.
U.S. Appl. No. 17/725,394, filed Apr. 20, 2022 Non-Final Office Action dated Jun. 25, 2025.
U.S. Appl. No. 17/731,155, filed Apr. 27, 2022 Non-Final Office Action dated Jul. 15, 2025.
U.S. Appl. No. 17/849,447, filed Jun. 24, 2022 Final Office Action dated May 7, 2025.
U.S. Appl. No. 17/863,211, filed Jul. 12, 2022 Final Office Action dated Jun. 3, 2025.
U.S. Appl. No. 17/945,875, filed Sep. 15, 2022 Notice of Allowance dated Jul. 21, 2025.
U.S. Appl. No. 18/075,280, filed Dec. 5, 2022 Non-Final Office Action dated Jun. 11, 2025.
U.S. Appl. No. 17/717,919, filed Apr. 11, 2022 Notice of Allowance dated Dec. 3, 2025.
U.S. Appl. No. 17/721,333, filed Apr. 14, 2022 Non-Final Office Action dated Oct. 16, 2025.
U.S. Appl. No. 17/725,394, filed Apr. 20, 2022 Final Office Action dated Nov. 19, 2025.
U.S. Appl. No. 17/849,447, filed Jun. 24, 2022 Ex Parte Quayle Action dated Sep. 4, 2025.
U.S. Appl. No. 17/849,447, filed Jun. 24, 2022 Notice of Allowance dated Nov. 19, 2025.
U.S. Appl. No. 17/863,211, filed Jul. 12, 2022 Advisory Action dated Sep. 11, 2025.
U.S. Appl. No. 17/863,211, filed Jul. 12, 2022 Notice of Allowance dated Oct. 22, 2025.
U.S. Appl. No. 18/075,280, filed Dec. 5, 2022 Final Office Action dated Nov. 19, 2025.
U.S. Appl. No. 17/721,333, filed Apr. 14, 2022 Notice of Allowance dated Feb. 24, 2026.
U.S. Appl. No. 17/725,394, filed Apr. 20, 2022 Advisory Action dated Jan. 13, 2026.
U.S. Appl. No. 17/731,155, filed Apr. 27, 2022 Final Office Action dated Feb. 9, 2026.
U.S. Appl. No. 18/075,280, filed Dec. 5, 2022 Advisory Action dated Jan. 23, 2026.

* cited by examiner

CONDUCTOR INCORPORATED FIBER ENABLED MEDICAL SYSTEMS

SUMMARY

Briefly summarized, embodiments of the present invention are directed to a placement system for tracking, placing, and monitoring an elongate medical device such as a catheter assembly or the like, inserted into a body of a patient. The placement system utilizes optical fiber-based strain sensors to ascertain information regarding the medical device during and/or after insertion into the patient's body and can further include one or more conductive elements extending therethrough.

In one embodiment, the placement system comprises a multi-core, fiber optic-based strain sensor (FOSS) system having a plurality of optical fiber-based strain sensors included within the elongate medical device. A laser light source (or other suitable light source) is also included and configured to operably connect with the strain sensors and produce outgoing optical signals incident on the strain sensors. A photodetector is included and configured to operably connect with the strain sensors and receive return optical signals from the strain sensors. A processor is configured to process data from the return optical signals. The data relates to an aspect of the medical device. A user interface such as a display is configured to communicate information relating to the aspect of the medical device.

The elongate medical device, including a multi-core optical fiber, can further include one or more conductive elements such as traces, wires, tubes, or the like, formed therewith. As used herein, a trace can include a thin layer or coating of conductive material disposed on a surface. The conductive elements can extend through the cladding of the optical fiber, through an insulator layer, or adhered to an outer surface of the elongate medical device, or combinations thereof. In an embodiment, the conductive elements can be one or more conductive tubes, or portions of the tubes, disposed annularly about the multi-core optical fiber.

In an embodiment, the conductive elements can be configured to transmit one or more electrical signals therealong from sensors at a distal tip of the medical device, to a console disposed proximally. This allows the fiber-optic enabled medical device to also detect one or more electrophysiological signals, such as temperature, pressure, oxygen saturation, optical signals, impedance signals, conductance signals, or the like. In an embodiment, the conductive elements can be configured to transmit electrical energy to the distal tip of the medical device, such as electro-stimulation signals, ablation energy, or the like. Advantageously, the conductive elements can further enhance the functionality of the fiber-optic enabled medical device.

Disclosed herein is a fiber-optically enabled medical system including, an elongate medical device extending longitudinally and having an optical fiber having one or more core fibers extending through a cladding layer, a first conductive element extending axially and configured to conduct an first electrical signal, a second conductive element extending axially and configured to conduct a second electrical signal, different from the first electrical signal, and an insulating layer disposed over one or both of the optical fiber and between the first conductive element and the second conductive element.

In some embodiments, one or both of the first conductive element and the second conductive element is one of a trace or a wire extending helically through one or both of the cladding layer and the insulating layer.

In some embodiments, the fiber-optically enabled medical system further includes a first trace or wire disposed at a first radius from a central axis, and a second trace or wire disposed at a second radius from the central axis, different from the first radius.

In some embodiments, one or both of the cladding layer and the insulating layer defines a microlumen in which one or both of the first conductive element and the second conductive element is disposed.

In some embodiments, one or both of the first conductive element and the second conductive element is a tube extending annularly about a central axis.

In some embodiments, the fiber-optically enabled medical system further includes a first tube disposed at a first radius and a second tube disposed at a second radius, different from the first radius.

In some embodiments, the fiber-optically enabled medical system further includes a second insulating layer disposed between the first tube and the second tube.

In some embodiments, one or both of the first conductive element and the second conductive element is a tube section extending about a central axis through an arc distance of between 90° and 180°.

In some embodiments, the fiber-optically enabled medical system further includes a first tube section disposed at a first radius and a second tube section disposed at a second radius, different from the first radius.

In some embodiments, the fiber-optically enabled medical system further includes a second insulating layer disposed between the first tube section and the second tube section.

In some embodiments, the fiber-optically enabled medical system further includes a sensor disposed at a distal tip of the elongate medical device and a console coupled to a proximal end of the elongate medical device, one or both of the first conductive element and the second conductive element providing an electrical pathway between the sensor and the console.

In some embodiments, the sensor is configured to detect one of a temperature, pressure, blood pressure, oxygen saturation, electro-optical signals, electrical impedance signals, or electrical conductance signals.

In some embodiments, one or both of the first conductive element and the second conductive element is configured to transmit one of an electro-stimulation signal energy or an ablation signal energy from a console coupled to a proximal end of the elongate medical device to a distal tip of the elongate medical device.

In some embodiments, the elongate medical device includes one of a stylet, trocar, guidewire, or catheter.

Also disclosed is a method of placing a catheter within a vasculature including, advancing a medical device assembly through the vasculature, the medical device assembly including an optical fiber and one or more conductive elements, detecting, by an optical modality of the optical fiber, a shape of the medical device assembly, detecting, by a first conductive element of the one or more conductive elements a location of the a distal tip of the medical device assembly by one or both of a TLS modality and an ECG modality, and detecting, by a second conductive element of the one or more conductive elements an electrophysiological signal.

In some embodiments, the one or more conductive elements is a trace or a wire extending linearly or helically through one or both of a cladding layer and an insulating layer of the optical fiber.

In some embodiments, the first conductive element is disposed at a first radius from a central axis, and the second conductive element is disposed at a second radius from the central axis, different from the first radius.

In some embodiments, one of the first conductive element or the second conductive element is a tube extending annularly about a central axis.

In some embodiments, one of the first conductive element or the second conductive element is a tube section extending about a central axis through an arc distance of between 90 o and 180 o.

In some embodiments, the electrophysiological signal includes one of a temperature, pressure, blood pressure, oxygen saturation, electro-optical signals, electrical impedance signals, or electrical conductance signals.

In some embodiments, the method further includes providing, by a third conductive element of the one or more conductive elements, one of an electro-stimulation signal or an ablation signal to the distal tip of the medical device assembly.

In some embodiments, the medical device assembly includes one or more of a stylet, a trocar, a guidewire, and a catheter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1:
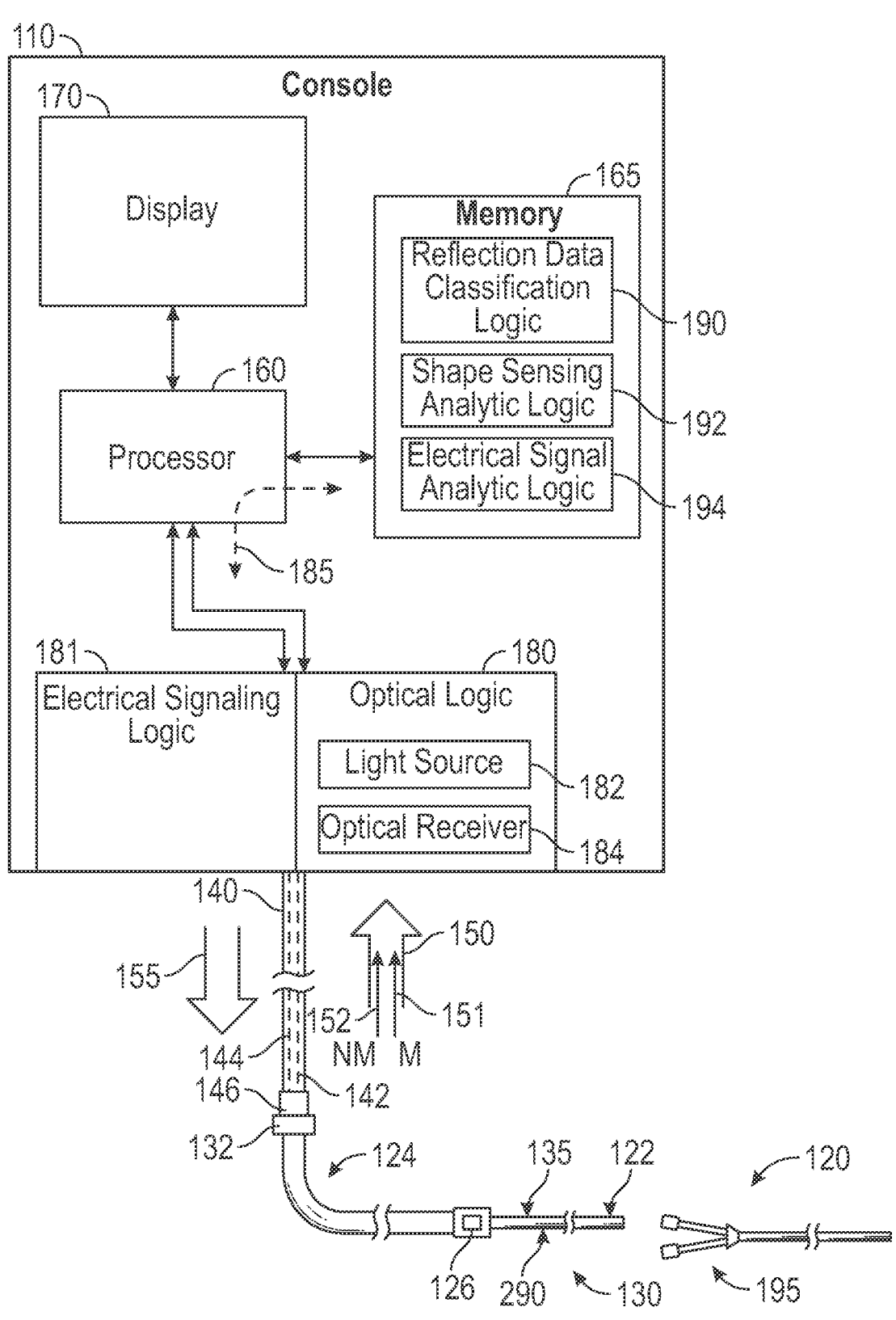
FIG. 1 shows a schematic view of a fiber optic-based strain sensor (FOSS) system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein. It is understood that the drawings are diagrammatic and schematic representations of exemplary embodiments of the invention, and are neither limiting nor necessarily drawn to scale.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

In the following description, the terms "or" and "and/or" as used herein are to be interpreted as inclusive or meaning any one or any combination. As an example, "A, B or C" or "A, B and/or C" mean "any of the following, A, B, C, A and B, A and C, B and C, A, B and C." An exception to this definition will occur only when a combination of elements, components, functions, steps or acts are in some way inherently mutually exclusive.

The term "logic" is representative of hardware and/or software that is configured to perform one or more functions. As hardware, logic may include circuitry having data processing and/or storage functionality. Examples of such circuitry may include, but are not limited or restricted to a processor, a programmable gate array, a microcontroller, an application specific integrated circuit, combinatorial circuitry, or the like. Alternatively, or in combination with the hardware circuitry described above, the logic may be software in the form of one or more software modules, which may be configured to operate as its counterpart circuitry. The software modules may include, for example, an executable application, a daemon application, an application programming interface (API), a subroutine, a function, a procedure, a routine, source code, or even one or more instructions. The software module(s) may be stored in any type of a suitable non-transitory storage medium, such as a programmable circuit, a semiconductor memory, non-persistent storage such as volatile memory (e.g., any type of random access memory "RAM"), persistent storage such as non-volatile memory (e.g., read-only memory "ROM", power-backed RAM, flash memory, phase-change memory, etc.), a solid-state drive, hard disk drive, an optical disc drive, or a portable memory device.

With respect to "proximal," a "proximal portion" or a "proximal end portion" of, for example, a stylet disclosed herein includes a portion of the stylet intended to be near a clinician when the stylet is used on a patient. Likewise, a "proximal length" of, for example, the stylet includes a length of the stylet intended to be near the clinician when the stylet is used on the patient. A "proximal end" of, for example, the stylet includes an end of the stylet intended to be near the clinician when the stylet is used on the patient. The proximal portion, the proximal end portion, or the proximal length of the stylet can include the proximal end of the stylet; however, the proximal portion, the proximal end portion, or the proximal length of the stylet need not include the proximal end of the stylet. That is, unless context suggests otherwise, the proximal portion, the proximal end portion, or the proximal length of the stylet is not a terminal portion or terminal length of the stylet.

With respect to "distal," a "distal portion" or a "distal end portion" of, for example, a stylet disclosed herein includes a portion of the stylet intended to be near or in a patient when the stylet is used on the patient. Likewise, a "distal length" of, for example, the stylet includes a length of the stylet intended to be near or in the patient when the stylet is used on the patient. A "distal end" of, for example, the stylet includes an end of the stylet intended to be near or in the patient when the stylet is used on the patient. The distal portion, the distal end portion, or the distal length of the stylet can include the distal end of the stylet; however, the distal portion, the distal end portion, or the distal length of the stylet need not include the distal end of the stylet. That is, unless context suggests otherwise, the distal portion, the distal end portion, or the distal length of the stylet is not a terminal portion or terminal length of the stylet.

Figure 2:
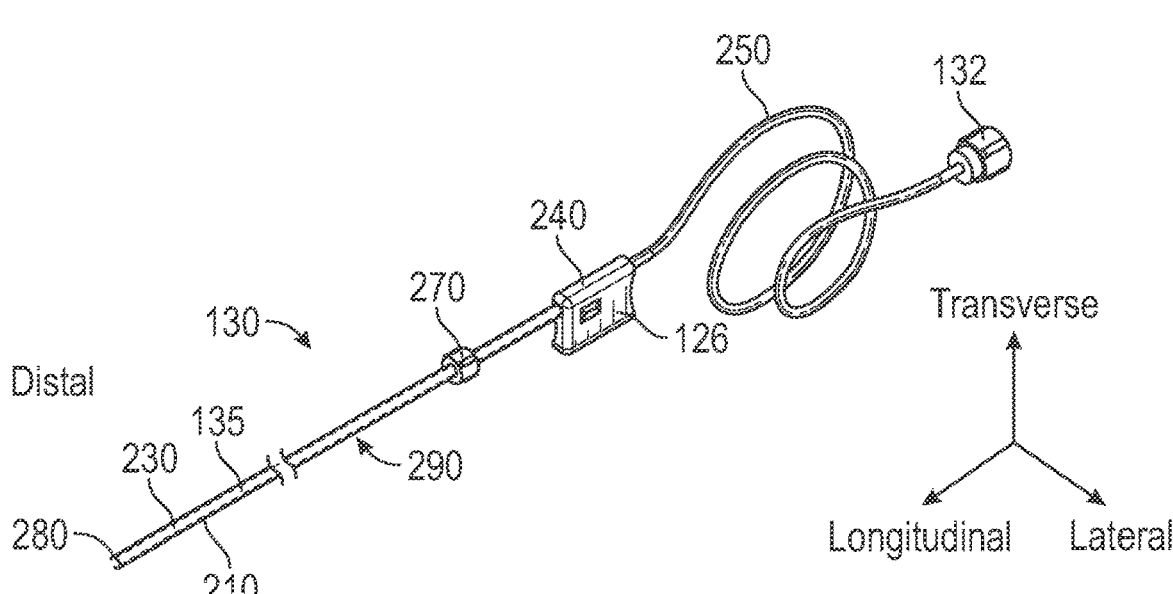
FIG. 2 shows a perspective view of a stylet assembly for use with the system of FIG. 1, in accordance with embodiments disclosed herein.

To assist in the description of embodiments described herein, as shown in FIG. 2, a longitudinal axis extends substantially parallel to an axial length of the stylet. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

It is important to note that, though the below discussion focuses on usage of a stylet for the placement of a catheter into the body of the patient, the stylet described herein can be employed to place a variety of medical devices, especially other elongate medical devices, in a variety of locations within the patient body. As such, the principles of the present disclosure should not be considered limiting to what is explicitly described herein. Examples of catheter assemblies and medical devices that may benefit from the disclosure may include a peripherally inserted central catheter ("PICC"), central venous catheter ("CVC"), urinary catheter, midline catheter, peripheral catheter, or the like.

In light of the above, a multi-core optical fiber can also be paired with one or more conductive elements for electrical signal monitoring thus serves multiple modalities. For example, the first modality constitutes an optical modality with shape sensing functionality to determine the physical state of the stylet, or similar elongate medical device. The physical state of the stylet provides information to assist a clinician in guiding a catheter assembly to a desired location within the vasculature.

The one or more second modalities can include but not limited to a tip location/navigation system ("TLS") modality, an ECG modality, electrophysiology measurements, such as temperature, pressure, blood pressure, oxygen saturation, electro-optical signals, electrical impedance signals, or electrical conductance signals, as well as electro-stimulation energy, ablation energy, or signal conductance. In an embodiment, a tip location/navigation system ("TLS") modality includes where the stylet with conductive element is advanced to detect and avoid any tip malposition during such advancement. In an embodiment, an ECG modality includes wherein ECG signal-based catheter tip guidance is employed to enable tracking and guidance of the stylet/catheter tip to a desired position with respect to a node of the patient's heart from which the ECG signals originate. Further details and embodiments of TLS and/or ECG modality systems can be found in U.S. Pat. Nos. 8,388,541, 8,971,994, 9,492,097, 9,636,031, 10,238,418, 10,966,630, 11,027,101, U.S. 2018/0116551, U.S. 2018/0304043, U.S. 2019/0069877, U.S. 2019/0099108, U.S. 2020/0054858, U.S. 2020/0237255, and U.S. 2020/0345983, each of which are incorporated by reference in their entirety.

Referring to FIG. 1, an illustrative embodiment of a medical device monitoring system ("system") 100 is shown. As shown, the system 100 generally includes a console 110 and a handheld, elongate medical device such as a stylet/catheter assembly 120 communicatively coupled to the console 110. It will be appreciated, however, that the stylet/catheter assembly 120 is exemplary and the stylet/catheter assembly 120 can include various stylets, trocars, guidewires, catheters, or combinations thereof. For this embodiment, the stylet/catheter assembly 120 includes a stylet assembly 130 coupled with a catheter assembly 195, as described in more detail herein.

In an embodiment, the stylet assembly 130 includes an elongate probe (e.g., stylet body) 290 on its distal end 122 and a console connector 132 on its proximal end 124. The console connector 132 enables the stylet assembly 130 to be operably connected to the console 110 via an interconnect 140 including one or more optical fibers 142 (hereinafter, "optical fiber(s)") and one or more conductive element 144, and terminated by one or more optical/electric connectors ("connector") 146. Herein, the connector 146 is configured to engage (mate) with the console connector 132 to allow for the propagation of light between the console 110 and the stylet assembly 130 as well as the propagation of electrical signals from the stylet 290 to the console 110.

An exemplary implementation of the console 110 includes a processor 160, a memory 165, a display 170 and one or more logic engines, e.g. optical logic 180. Although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Pat. No. 10,992,078, the entire contents of which are incorporated by reference herein. The processor 160, with access to the memory 165 (e.g., non-volatile memory), is included to control functionality of the console 110 during operation. As shown, the display 165 may be a liquid crystal diode (LCD) display integrated into the console 110 and employed as a user interface to display information to the clinician, especially during a catheter placement procedure (e.g., cardiac catheterization). In another embodiment, the display 165 may be separate from the console 110. Although not shown, a user interface is configured to provide user control of the console 110.

For both of these embodiments, the content depicted by the display 165 may change according to which mode the stylet assembly 130 is configured to operate, e.g. optical, TLS, ECG, electrophysiological sensors, electro-stimulation, ablation, or other modality. In TLS mode, the content rendered by the display 165 may constitute a two-dimensional (2-D) or three-dimensional (3-D) representation of the physical state (e.g., length, shape, form, and/or orientation) of the stylet 290 computed from characteristics of reflected light signals 150 returned to the console 110. The reflected light signals 150 constitute light of a specific spectral width of broadband incident light 155 reflected back to the console 110. According to one embodiment of the disclosure, the reflected light signals 150 may pertain to various discrete portions (e.g., specific spectral widths) of broadband incident light 155 transmitted from and sourced by the optical logic 180, as described below.

According to one embodiment of the disclosure, an activation control 126, included on the stylet assembly 130, may be used to set the stylet 290 into a desired operating mode and selectively alter operability the display 165 by the clinician to assist in medical device placement. For example, based on the modality of the stylet 290, the display 165 of the console 110 can be employed for optical modality-based guidance during catheter advancement through the vasculature or TLS modality to determine the physical state (e.g., length, form, shape, orientation, etc.) of the stylet 290. In one embodiment, information from multiple modes, such as optical, TLS, ECG, electrophysiological sensors, electro-stimulation, etc., may be displayed concurrently (e.g., at least partially overlapping in time). In one embodiment, the display 165 is a liquid crystal diode (LCD) device or touch screen device.

Referring still to FIG. 1, the optical logic 180 is configured to support operability of the stylet assembly 130 and enable the return of information to the console 110, which may be used to determine the physical state associated with the stylet 290 along with monitored electrical signals, such as ECG signaling, electrophysiological sensors, etc., via an electrical signaling logic 181 that supports receipt and processing of the received electrical signals from the stylet 290 (e.g., ports, analog-to-digital conversion logic, etc.). The physical state of the stylet 290 may be based on changes in characteristics of the reflected light signals 150 received from the stylet 290. The characteristics may include shifts in wavelength caused by strain on certain regions of the core fibers integrated within a multi-core optical fiber 135 positioned within or operating as the stylet 290, as shown below. From information associated with the reflected light signals 150, the console 110 may determine (through computation or extrapolation of the wavelength shifts) the physical state of the stylet 290, and notably a catheter assembly 195 configured to receive the stylet 290.

According to one embodiment of the disclosure, as shown in FIG. 1, the optical logic 180 may include a light source 182 and an optical receiver 184. The light source 182 is configured to transmit the broadband incident light 155 for propagation over the optical fiber(s) 142 included in the interconnect 140, which are optically connected to the multi-core optical fiber 135 within the stylet 290. In one embodiment, the light source 182 is a tunable swept laser, although other suitable light source can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the multi-core optical fiber 135 deployed within the stylet 290 (see FIGS. 2 and 5), and (ii) translate the reflected light signals 150 into reflection data 185, namely data in the form of electrical signals representative of the reflected light signals including wavelength shifts caused by strain. The reflected light signals 150 associated with different spectral widths may include reflected light signals 151 provided from sensors positioned in the center core fiber, e.g. center core fiber $510_1$, of the multi-core optical fiber 135 and reflected light signals 152 provided from sensors positioned in the periphery core fibers, e.g. periphery core fibers $510_{1-4}$, of the multi-core optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the processor 160, which governs their operation. Also, the optical receiver 184 is operably coupled to provide the reflection data 185 to the memory 165 for storage and processing by reflection data classification logic 190. The reflection data classification logic 190 may be configured to: (i) identify which core fibers pertain to which of the received reflection data 185 and (ii) segregate the reflection data 185 provided from reflected light signals 150 pertaining to similar regions of the stylet 290 or spectral widths into analysis groups. The reflection data for each analysis group is made available to shape sensing analytic logic 192 for analytics.

According to one embodiment of the disclosure, the shape sensing analytic logic 192 is configured to compare wavelength shifts measured by sensors deployed in each periphery core fiber at the same measurement region of the stylet 290 (or same spectral width) to the wavelength shift at a center core fiber of the multi-core optical fiber 135 positioned along central axis and operating as a neutral axis of bending. From these analytics, the shape sensing analytic logic 192 may determine the shape the core fibers have taken in 3-D space and may further determine the current physical state of the catheter assembly 195 in 3-D space for rendering on the display 170.

According to one embodiment of the disclosure, the shape sensing analytic logic 192 may generate a rendering of the current physical state of the stylet 290 (and potentially the catheter assembly 195), based on heuristics or run-time analytics. For example, the shape sensing analytic logic 192 may be configured in accordance with machine-learning techniques to access a data store (library) with pre-stored data (e.g., images, etc.) pertaining to different regions of the stylet 290 (or catheter assembly 195) in which reflected light from core fibers have previously experienced similar or identical wavelength shifts. From the pre-stored data, the current physical state of the stylet 290 (or catheter assembly 195) may be rendered. Alternatively, as another example, the shape sensing analytic logic 192 may be configured to determine, during run-time, changes in the physical state of each region of the multi-core optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the multi-core optical fiber 135 to the wavelength shift generated by a sensor of the center core fiber at the same cross-sectional region. It is contemplated that other processes and procedures may be performed to utilize the wavelength shifts as measured by sensors along each of the core fibers within the multi-core optical fiber 135 to render appropriate changes in the physical state of the stylet 290 (and/or catheter assembly 195), especially to enable guidance of the stylet 290, when positioned at a distal tip of the catheter assembly 195, within the vasculature of the patient and at a desired destination within the body.

The console 110 may further include electrical signal receiver logic 186, which is positioned to receive one or more electrical signals from the stylet 290. In an embodiment, the stylet 290 is configured to support both optical connectivity as well as electrical connectivity. The electrical signal receiver logic 186 is configured to send or receive the electrical signals or electrical energy to/from the stylet 290 via the conductive element 144, 230.

In an embodiment, the conductive elements, or medium, 230 of the stylet 290 can transfer electrical signals from one or more sensors disposed at a distal tip of the stylet 290 to the console 110 for processing by the electrical signal analytic logic 194, executed by the processor 160. Such electrical signals can indicate body temperature, blood pressure, oxygen saturation, light, electrical impedance, electrical conductance, combinations thereof, or the like at a distal tip of the stylet 290. Alternatively, or in addition to, the electrical signal analytic logic 194 can send electrical energy signals by way of the conductive element 230 to a distal tip of the stylet 290 for electrical stimulation or ablation at a target location. Advantageously, the one or more conductive elements 230 can provide increased functionality to the fiber-enabled medical device 130.

Referring now to FIG. 2, an exemplary embodiment of the stylet assembly 130 to be operably connected to the catheter assembly 195 (FIG. 3) is shown. Herein, the stylet assembly 130 features the stylet 290, which includes an insulating layer 210 encasing a multi-core optical fiber 135 and/or one or more conductive element 230 as shown in FIGS. 6A-11B and described below. The stylet 290 extends distally from a handle 240 while an interconnect (e.g. tether) 250 extends proximally from the handle 240 and is terminated by the console connector 132 for coupling to the interconnect 140 of the console 110 as shown in FIG. 1. The handle 240 is included with the second interconnect (e.g., tether) 250 to assist with manipulation of the stylet 290 by the user during operation and may be configured to include activation controls 126.

As shown, the stylet 290 and the interconnect 250 provide a pathway for outgoing optical signals produced by the light source 182 of the optical logic 180 and returning optical signals, produced by gratings within the core fibers of the multi-core optical fiber 135, for receipt by the photodetector 184 (see FIG. 1). Insulating layers associated with the stylet 290 and the interconnect 250 may vary in density and material to control its rigidity and mechanical properties, as described herein.

Figure 3:
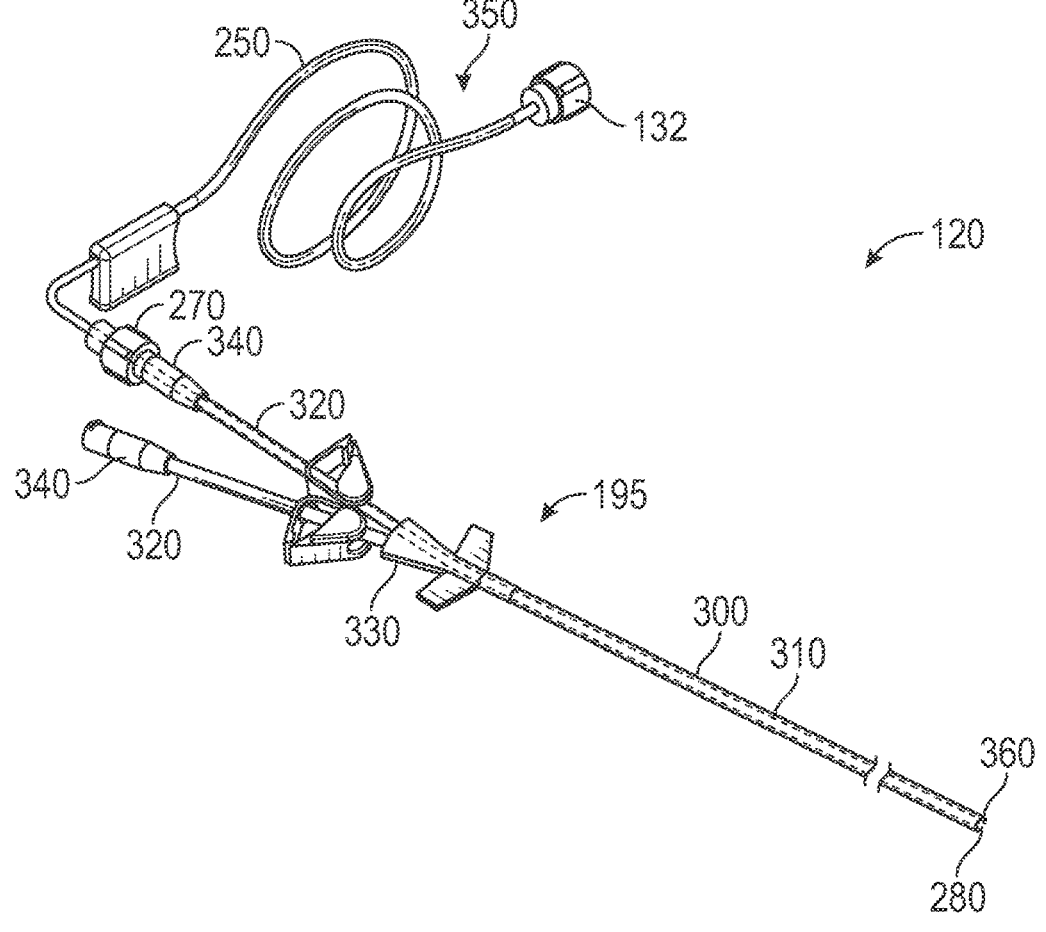
FIG. 3 shows a perspective view of a stylet and catheter assembly for use with the system of FIG. 1, in accordance with embodiments disclosed herein.

Furthermore, according to one embodiment of the disclosure, the stylet assembly 130 further includes a catheter connector 270, which may be threaded for attachment to a connector of an extension leg of a catheter assembly 195 (see FIG. 3). This connectivity between the connector 270 and a connector of the extension leg connector may be used during the procedure of inserting the stylet 290 into a lumen of the catheter assembly 195, as shown in FIG. 3. When deployed, a distal end of the multi-core optical fiber 135 need not be substantially co-terminal with a distal tip 360 of the catheter assembly 195. As will be seen, the returned optical signals (reflected light 150) from the sensors (reflective gratings) within each core fiber included with the multi-core optical fiber 135 may be analyzed during its advancement through the patient vasculature.

Note further that, it should appreciated that the term "stylet," as used herein, can include any one of a variety of devices configured for removable placement within a lumen of the catheter (or other portion of a medical device) to assist in placing a distal end of the catheter in a desired location within the patient's vasculature. Also, note that other connection schemes between the stylet 290 and the console 110 can also be used without limitation.

Referring to FIG. 3, an embodiment of the stylet assembly 130 for placement within the catheter assembly 195 to provide a stylet/catheter assembly 120 is shown. Herein, the catheter assembly 195 includes an elongate catheter tube 300 defining one or more lumens 310 extending between proximal and distal ends of the catheter tube 300. The catheter tube 300 is in communication with a corresponding extension leg 320 via a bifurcation hub 330. Luer connectors 340 are included on the proximal ends of the extension legs 320.

As shown, the stylet assembly 130 includes the console connector 132 on its proximal end 350 to enable the stylet 290 to operably connect with the console 110 (see FIG. 1). The interconnect 250 distally extends communications from the console 110 to the catheter connector 270, which is configured to threadably engage (or otherwise connect with) the Luer connector 340 of one of the extension legs 320 of the catheter assembly 195. The stylet 290 extends distally from the catheter connector 270 up to a distal-end 280 of the stylet 290. The distal-end 280 of the stylet 290 may be substantially co-terminal with a distal tip 360 of the catheter assembly 195 within the vasculature.

Figure 4:
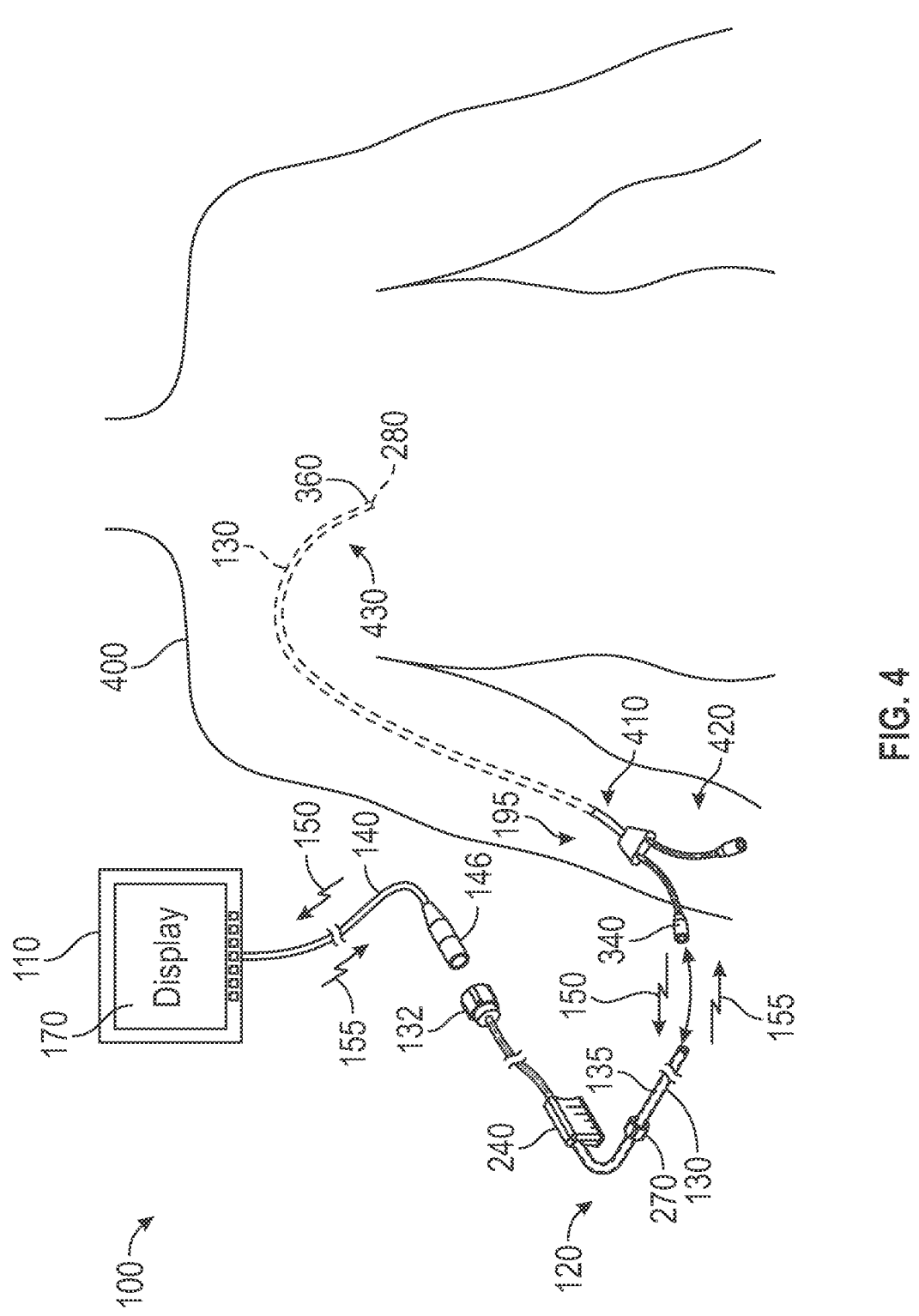
FIG. 4 shows the system of FIGS. 1-3 including a stylet and catheter assembly inserted into a vasculature of a patient, in accordance with embodiments disclosed herein.

Referring now to FIG. 4, an embodiment of the stylet 290 illustrating its placement within the catheter assembly 195 as the catheter assembly 195 is being inserted into a vasculature of a patient 400 through a skin insertion site 410 is shown. As illustrated in FIG. 4, the catheter assembly 195 generally includes a proximal portion 420 that generally remains exterior to the patient 400 and a distal portion 430 that generally resides within the patient vasculature after placement is complete. The stylet 290 is employed to assist in the positioning of the distal tip 360 of the catheter assembly 195 in a desired position within the patient vasculature. In one embodiment, the desired position for the catheter distal tip 360 is proximate the patient's heart, such as in the lower one-third ($\frac{1}{3}^{rd}$) portion of the Superior Vena Cava ("SVC") for this embodiment. Of course, the stylet 290 can be employed to place the catheter distal tip 360 in other locations.

Figure 5:
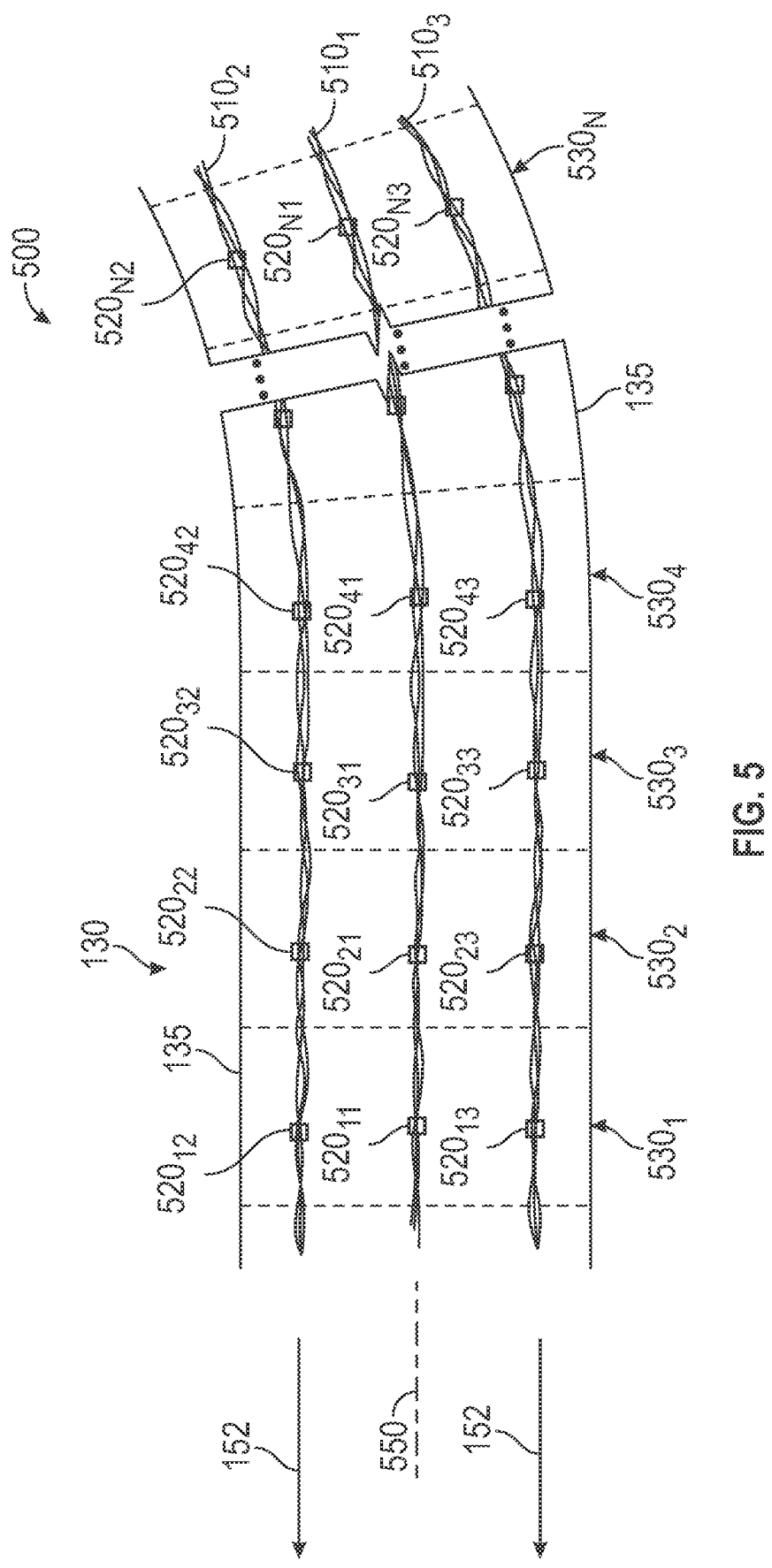
FIG. 5 shows an exemplary structure of a section of the multi-core optical fiber included within the stylet assembly of FIGS. 1-3, in accordance with embodiments disclosed herein.

During advancement of the catheter assembly 195, the stylet 290 receives broadband light 155 from the console 110 via interconnect 140, which includes the connector 146 for coupling to the console connector 132 for the stylet assembly 130. The reflected light 150 from sensors (reflective gratings) within each core fiber of the multi-core optical fiber 135 are returned from the stylet 290 over the interconnect 140 for processing by the console 110. The physical state of the stylet 290 may be ascertained based on analytics of the wavelength shifts of the reflected light 150. For example, the strain caused through bending of the stylet 290, and hence angular modification of each core fiber, causes different degrees of deformation. The different degrees of deformation alters the shape of the sensors (reflective grating) positioned on the core fiber, which may cause variations (shifts) in the wavelength of the reflected light from the sensors positioned on each core fiber within the multi-core optical fiber 135, as shown in FIG. 5. From this wavelength shifting, the shape sensing analytic logic 192 within the console 110 (see FIG. 1) may determine the physical state of the stylet 290 (e.g., shape, orientation, etc.).

Referring to FIG. 5, an exemplary embodiment of a right-sided, longitudinal view of a section 500 of the multi-core optical fiber 135 included within the stylet 290 is shown. The multi-core optical fiber section 500 depicts certain core fibers $510_1$-$510_M$ (M≥2, M=4 as shown) along with the spatial relationship between sensors (e.g., reflective gratings) $520_{11}$-$520_{NM}$ (N≥2; M≥2) present within the core fibers $510_1$-$510_M$, respectively. As shown, the section 500 is subdivided into a plurality of cross-sectional regions $530_1$-$530_N$, where each cross-sectional region $530_1$-$530_N$ corresponds to reflective gratings $520_{11}$-$520_{14}$ . . . $520_{M}$-$520_{N4}$. Some or all of the cross-sectional regions $530_1$ . . . $530_N$ may be static (e.g., prescribed length) or may be dynamic (e.g., vary in size among the regions $530_1$ . . . $530_N$). A first core fiber $510_1$ is positioned substantially along a center (neutral) axis 550 while core fiber $510_2$ may be oriented within the cladding 600 of the multi-core optical fiber 135, from a cross-sectional, front-facing perspective, to be position on "top" the first core fiber $510_1$. In this deployment, the core fibers $510_3$ and $510_4$ may be positioned "bottom left" and "bottom right" of the first core fiber 510i. (See FIG. 6B).

Referencing the first core fiber $510_1$ as an illustrative example, when the stylet 290 is operative, each of the reflective gratings $520_1$-$520_N$ reflect light for a different spectral width. As shown, each of the gratings $520_{1i}$-$520_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $510_2$-$510_3$ but along at the same cross-sectional regions $530$-$530_N$ of the multi-core optical fiber 135, the gratings $520_{12}$-$520_{N2}$ and $520_{13}$-$520_{N3}$ are configured to reflect incoming light at same (or substantially similar) center frequency. As a result, the reflected light returns information that allows for a determination of the physical state of the optical fiber 135 (and the stylet 290) based on wavelength shifts measured from the returned, reflected light. In particular, strain (e.g., compression or tension) applied to the multi-core optical fiber 135 (e.g., at least core fibers $510_2$-$510_3$) results in wavelength shifts associated with the returned, reflected light.

Based on different locations, the core fibers $510_1$-$510_4$ experience different types and degree of strain based on angular path changes as the stylet 290 advances in the patient.

For example, with respect to the multi-core optical fiber section 500 of FIG. 5, in response to angular (e.g., radial) movement of the stylet 290 is in the left-veering direction, the second core fiber $510_2$ of the multi-core optical fiber 135 with the shortest radius during movement (e.g., core fiber closest to a direction of angular change) would exhibit compression (e.g., forces to shorten length). At the same time, the third core fiber $510_3$ with the longest radius during movement (e.g., core fiber furthest from the direction of angular change) would exhibit tension (e.g., forces to increase length). As these forces are different and unequal, the reflected light from reflective gratings $520_{N2}$ and $520_{N3}$ associated with the core fiber $510_2$ and $510_3$ will exhibit different changes in wavelength. The differences in wavelength shift of the reflected light signals 152 can be used to extrapolate the physical configuration of the stylet 290 by determining the degrees of wavelength change caused by compression/tension for each of the periphery fibers (e.g., the second core fiber $510_2$, the third core fiber $510_3$, and the fourth core fiber $510_4$) in comparison to the wavelength of the reference core fiber (e.g., first core fiber $510_1$) located along the neutral axis 550 of the multi-core optical fiber 135. These degrees of wavelength change may be used to extrapolate the physical state of the stylet 290.

Further details, examples and embodiments of fiber-optic enabled strain sensor (FOSS) systems can be found in U.S. 2018/0289927, U.S. 2021/0045814, U.S. 2021/0156676, U.S. 2021/0154440, U.S. 2021/0275257, U.S. 2021/0268229, U.S. 2021/0271035, U.S. 2021/0402144, U.S. 2021/0401509, U.S. 2022/0011192, and U.S. 2022/0034733, each of which are incorporated by reference in their entirety.

Figure 6B:
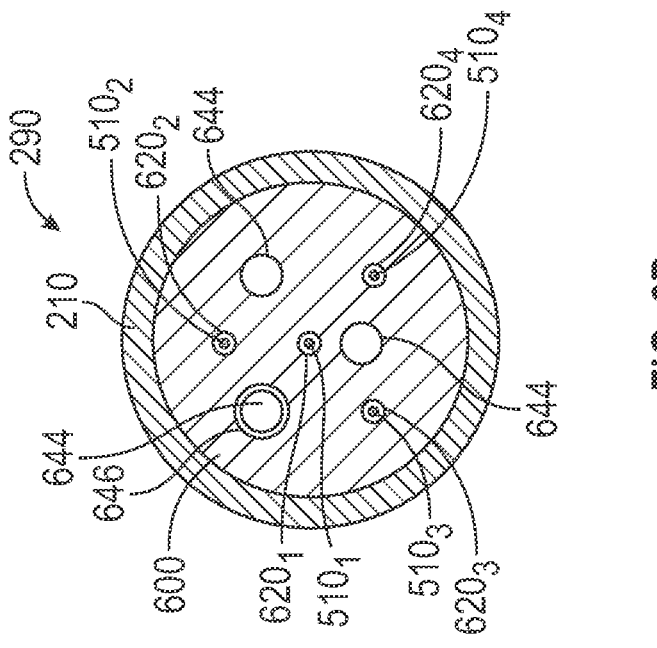
FIG. 6B shows a cross-section view of the multimodal stylet of FIG. 6A, in accordance with embodiments disclosed herein.
Figure 6A:
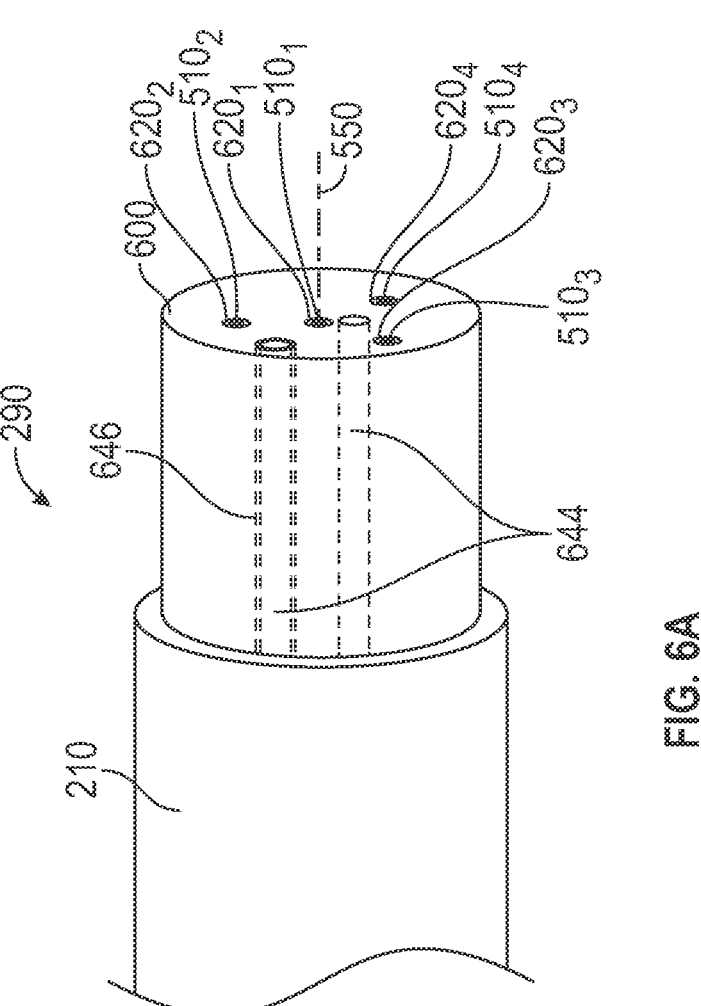
FIG. 6A shows a perspective view of a multimodal stylet including a conducting element, in accordance with embodiments disclosed herein.

Referring now to FIG. 6A, an exemplary embodiment of a multimodal stylet 290 of FIG. 1 supporting one or both of an optical and electrical signaling is shown. Herein, the stylet 290 features a centrally located multi-core optical fiber 135, which includes a cladding 600 and a plurality of core fibers $510_1$-$510_M$ (M≥2; M=4) residing within a corresponding plurality of lumens $620_1$-$620_M$. While the multi-core optical fiber 135 is illustrated within four (4) core fibers $510_1$-$510_4$, a greater number of core fibers $510_1$-$510_M$ (M>4) may be deployed to provide a more detailed three-dimensional sensing of the physical state (e.g., shape, orientation, etc.) of the multi-core optical fiber 135 and the stylet 290 deploying the optical fiber 135, a greater number of core fibers $510_1$-$510_M$ (M>4) may be deployed.

In an embodiment, the optical fiber 135 can include an insulating layer 210 disposed on an outer surface thereof. In an embodiment, the optical fiber 135 can include one or more conductive elements 230 extending through the optical fiber 135. Exemplary conductive elements 230 traces or wires 644, which can include one or more single core or multi core, woven or non-woven traces or wires 644, extending through the cladding 600 of the optical fiber 135 and/or through the insulating layer 210. As shown the wires 644 can extend through the optical fiber 135 parallel with the central axis 550 of the stylet 290. In an embodiment, the conductive element 230 (e.g. wire 644) can be formed of a conductive material such as a conductive plastic, conductive polymer, conductive epoxy, metal, alloy, or the like.

In an embodiment, the wires 644 can be radially dispersed, regularly or irregularly, about the central axis 550. In an embodiment, each wire 644 can be disposed at the same radius from the central axis 550 or at different radii from the central axis 550. In an embodiment, the wire(s) 644 can be co-extruded with the cladding 600 and/or core fibers 510 of the optical fiber 135. In an embodiment, the cladding 600 can define a micro-lumen 646 in which the electrically conductive wire 644 can be disposed. In an embodiment, the micro-lumen 646 can include an insulating lining disposed between the wire 644 and the cladding 600.

In an embodiment, each of the wire(s) 644 can coupled with one or more sensors disposed distally on the stylet 290, e.g. at a distal tip 280, or at a portion disposed proximally of the distal tip 280. The wire(s) 644 can communicatively couple the one or more sensors with the console 110 and can be configured to sense, ablate, transmit, detect, or stimulate depending on the desired application.

Figure 7B:
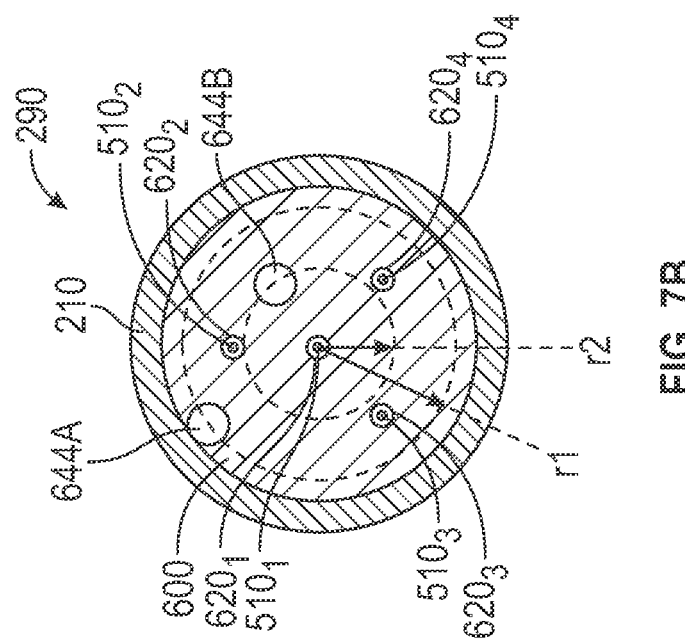
FIG. 7B shows a cross-section view of the multimodal stylet of FIG. 7A, in accordance with embodiments disclosed herein.
Figure 7A:
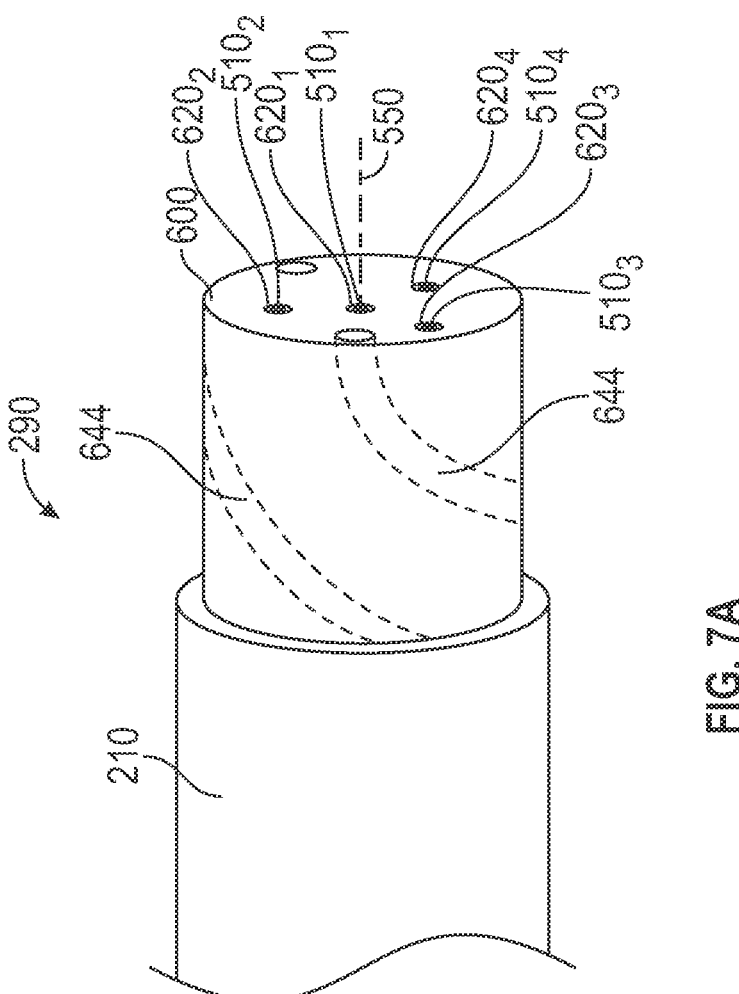
FIG. 7A shows a perspective view of a multimodal stylet including a multi-layer conducting element, in accordance with embodiments disclosed herein.

In an embodiment, as shown in FIGS. 7A-7B, the one or more wires 644 can extend through the cladding 600 in a spiral or helical arrangement, about the central axis 550. In an embodiment, each of the wires 644 can extend in a spiral arrangement at the same radius from the central axis 550. In an embodiment, each of the wires 644 can extend in a spiral arrangement at different radii from the central axis 550. For example, a first wire 644A can extend in a spiral at a first radius (r1) from the central axis 550, and a second wire 644B can extend in a spiral at a second radius (r2) from the central axis 550, less than the first radius (r1). As such, the conductive wires 644 can provide one or more layers extending through the cladding 660. In an embodiment, the thickness of the wires 644, the radius (r) of rotations, the numbers of wires 644 at each radius (r), the direction of the rotation (e.g. clockwise or counter clockwise), the density of rotations per longitudinal length, or combinations thereof can vary along the length of the optical fiber 135. Advantageously, the various numbers and configurations of the wire(s) 644 can further modify the mechanical properties (e.g. sheer strength, flexibility, rigidity, columnar strength, etc.) of the optical fiber 135 and/or stylet 290.

Figure 7D:
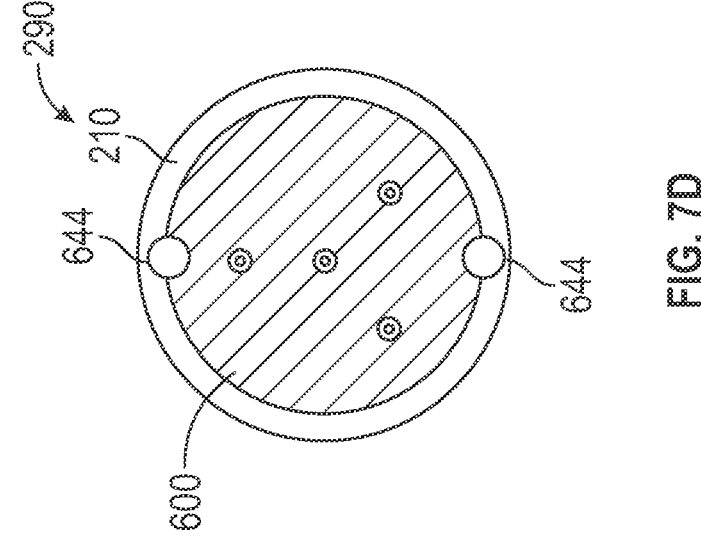
FIG. 7D shows a cross-section view of the multimodal stylet of FIG. 7C, in accordance with embodiments disclosed herein.
Figure 7C:
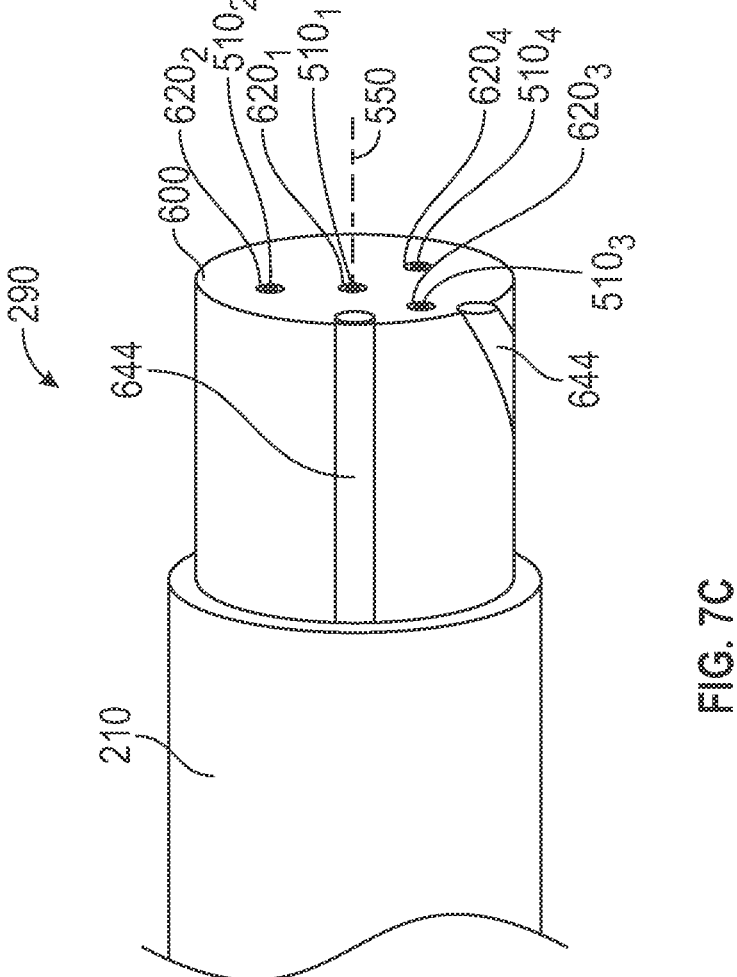
FIG. 7C shows a perspective view of a multimodal stylet including a multi-layer conducting element, in accordance with embodiments disclosed herein.

In an embodiment, as shown in FIGS. 7C-7D, the optical fiber 135 can include a combination of linear wires 644 (FIGS. 6A-6B) and helically arranged wires 644 (FIGS. 7A-7B), as described herein. In an embodiment, the traces or wire(s) 644 can extend, either linearly or helically, along surface of the cladding 600. In an embodiment, a portion of the wire 644 can be disposed within the cladding 600. For example, a cross-section center point of the wire 644 is aligned with a perimeter of the cladding 600. Optionally, the optical fiber 135 can include the insulating layer 210 disposed thereover, as such a portion of the wire 644 can be disposed within the insulating layer 210. In an embodiment the conductive element 230 can be a trace disposed on a surface of an insulating layer 210 and/or the cladding 600 and can extend linearly and/or helically, similar to that of the wire 644, as described herein. Each trace or wire 644 can be dedicated to one or more functions of electrophysiological signals, electro-stimulation signals, ablation, or the like, as described herein.

Figure 8B:
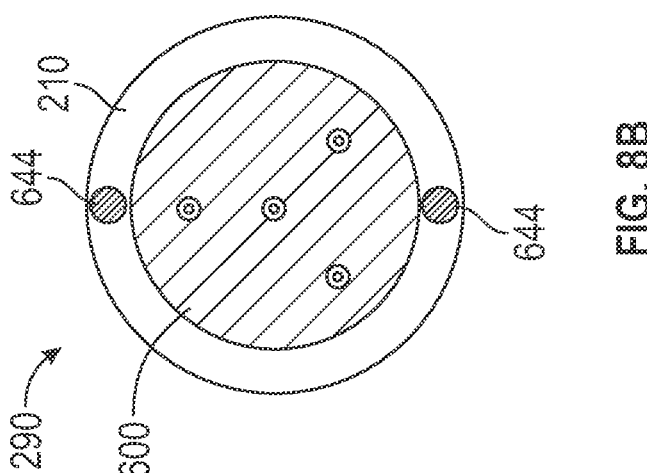
FIG. 8B shows a cross-section view of the multimodal stylet of FIG. 8A, in accordance with embodiments disclosed herein.
Figure 8A:
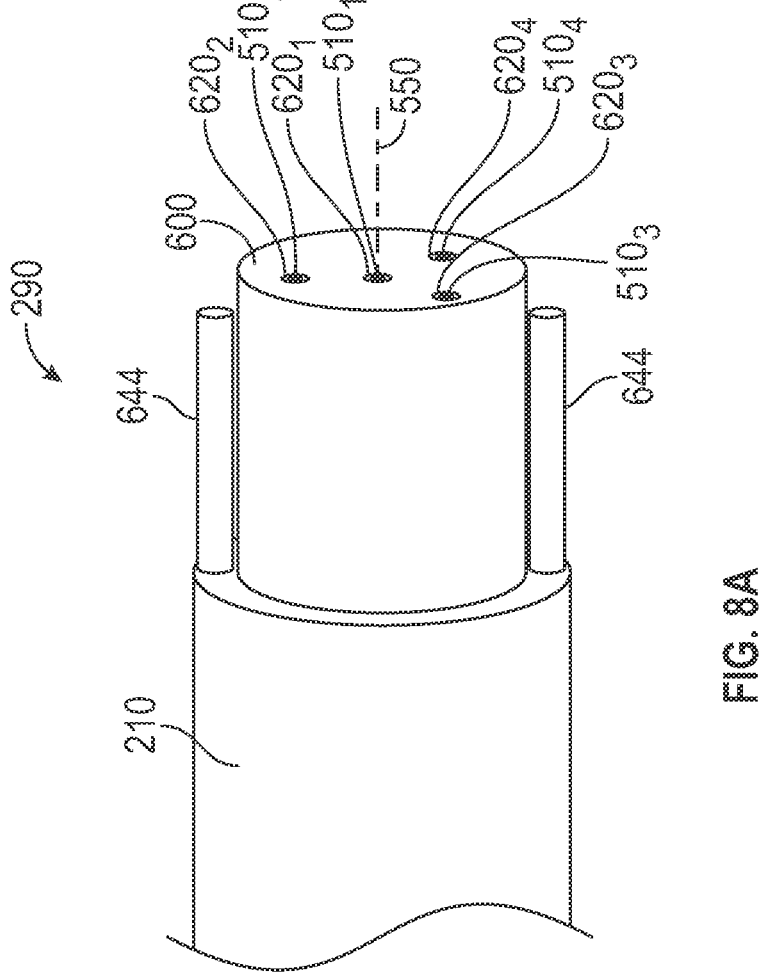
FIG. 8A shows a perspective view of a multimodal stylet including a conducting element disposed within a non-conductive layer, in accordance with embodiments disclosed herein.

In an embodiment, as shown in FIGS. 8A-8B, the optical fiber 135 can include one or more conductive elements 230 (e.g. trace or wire 644), extending through the insulating layer 210 disposed on an outer surface of the cladding 600. In an embodiment, the wire(s) 644 can extend linearly and/or helically through the insulating layer 210, as described herein. In an embodiment, the wire(s) 644 can vary in number, thickness (gauge), radius (r) of rotations, the numbers of wires 644 at each radius (r), the direction of the rotation (e.g. clockwise or counter clockwise), the density of rotations per longitudinal length, or combinations thereof along the length of the optical fiber 135, as described herein. Advantageously, the wire(s) 644 extending through the insulating layer 210 can modify the mechanical properties of the optical fiber 135 and/or stylet 290. Each wire 644 can be dedicated to one or more functions of electrophysiological signals, electro-stimulation signals, ablation, or the like, as described herein.

In an embodiment, the one or more conductive elements 230 can include a conductive tube 744 extending annularly about the central axis 550. In an embodiment, one or more conductive tubes 744 can be arranged concentrically about the central axis 550 and can extend through the cladding 600, the insulating layer 210, or both, i.e. a portion of the tube 744 can extend through the cladding 600 and a portion of the tube 744 can extend through the insulating layer 210. In an embodiment, a portion of the conductive tube 744 can extend between one or more core fibers 550. For example, the conductive tube 744 can extend about the central (neutral) core fiber 5501 and be disposed closer to the central axis 550 than the one or more peripheral core fibers, e.g. core fibers 550₂-550₄).

Figures 9A, 9B:
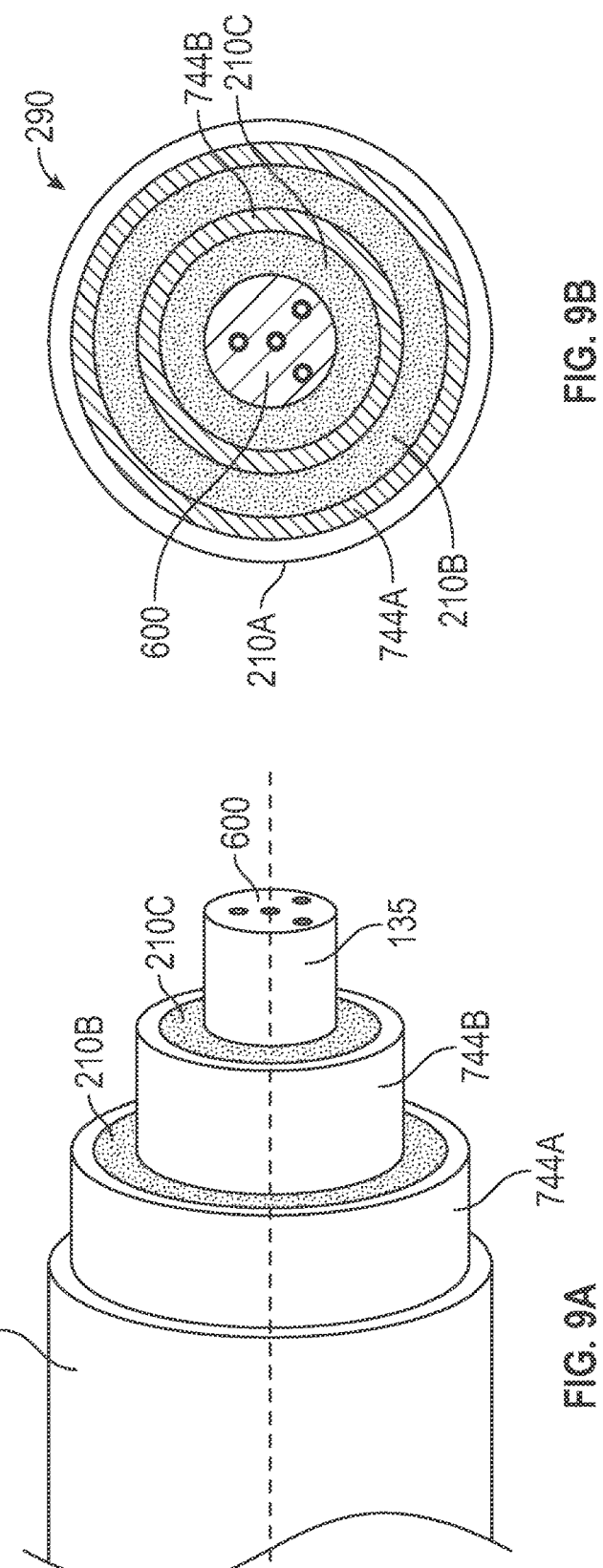
FIG. 9A shows a perspective view of a multimodal stylet including concentrically arranged conducting elements, in accordance with embodiments disclosed herein.
FIG. 9B shows a cross-section view of the multimodal stylet of FIG. 9A, in accordance with embodiments disclosed herein.

In an embodiment, the conductive tube(s) 744 can include one or more insulating layers disposed therebetween. For example, as shown in FIG. 9B, a first insulating layer 210A can be disposed outermost, on an outer surface of a first conductive tube 744A. A second insulating layer 210B can be disposed between the first conductive tube 744A and a central axis 550. In an embodiment, a second conductive tube 744B can be disposed within the first conductive tube 744B and can include a third insulating layer 210C between the second conductive tube 744B and the central axis 550. These and other numbers and combinations of conductive tubes 744 and insulating layers 210 are contemplated to fall within the scope of the present invention.

In an embodiment, the conductive tube 744 can be formed of a conductive material such as a conductive plastic, conductive polymer, conductive epoxy, metal, alloy, or the like. In an embodiment, the conductive tube 744 can be formed as a solid-walled tube. In an embodiment, the conductive tube 744 can be formed of one or more strands of woven or non-woven conductive material.

Figure 10B:
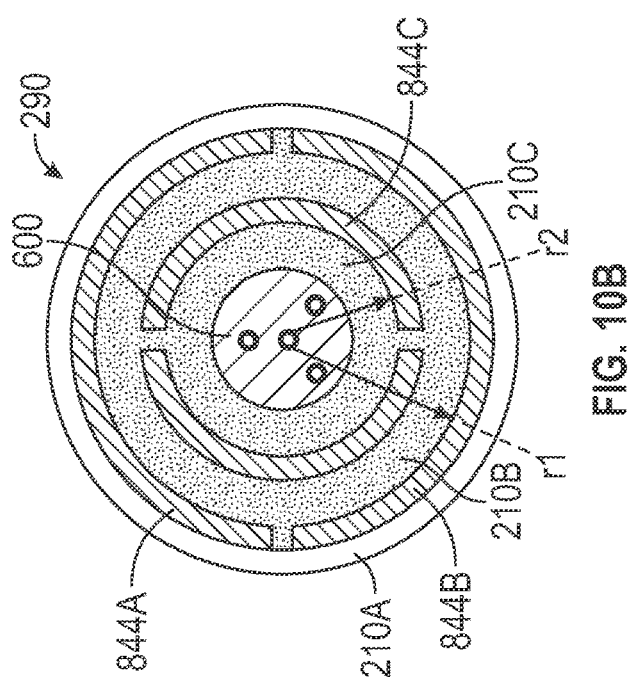
FIG. 10B shows a cross-section view of the multimodal stylet of FIG. 10A, in accordance with embodiments disclosed herein.
Figure 10A:
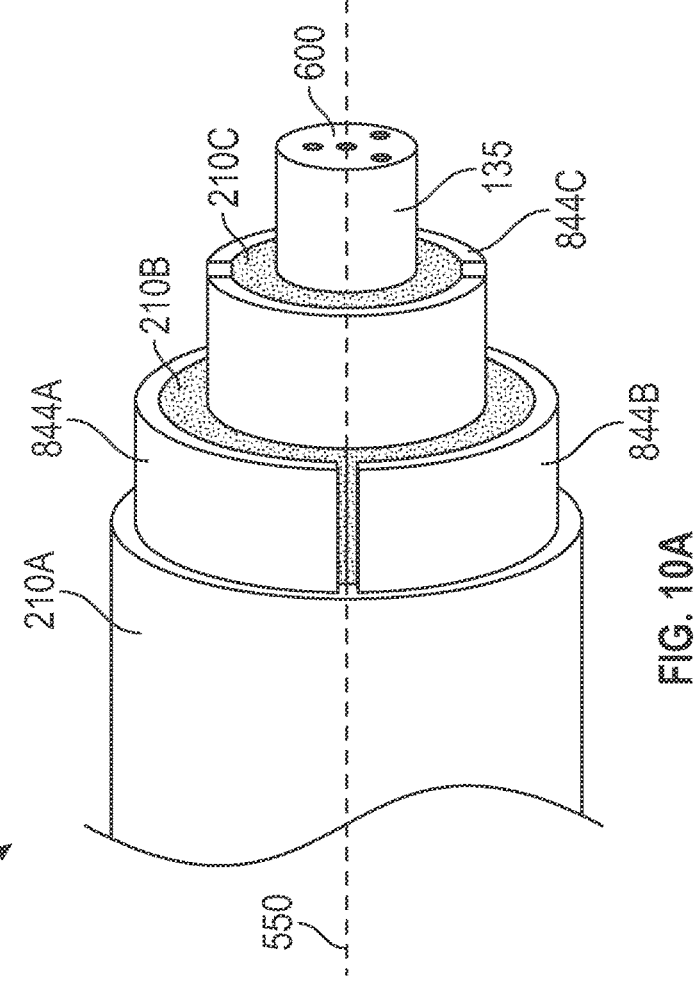
FIG. 10A shows a perspective view of a multimodal stylet including concentrically arranged sections of conducting elements, in accordance with embodiments disclosed herein.

In an embodiment, as shown in FIGS. 10A-10B, the optical fiber 135 can include a conductive element 230 extending about a central axis 550 through an arc distance of less than 360°. For example, the optical fiber 135 can include a conductive tube section 844 extending through an arc distance of between 1° and 359°. As shown, the conductive tube section 844 can extend through an arc distance 180°. However, it will be appreciated that other arc distances which are lesser or greater than 180° (e.g. 90°, 120°, etc.) are also contemplated.

In an embodiment, the optical fiber 135 can include one or more conductive tube section(s) 844, e.g. a first conductive tube section 844A and a second conductive tube section 844B, extending about the central axis 550. The first conductive tube section 844A and the second conductive tube section 844B can extend through the same arc distance or through different arc distances. In an embodiment, the optical fiber 135 can include one or more conductive tube section(s) 844 disposed at the same radius from the central axis 550. For example, the first conductive tube section 844A and the second conductive tube section 844B can both be disposed at the same radius (r1).

In an embodiment, the optical fiber 135 can include one or more conductive tube section(s) 844 disposed at different radii from the central axis 550. For example, the first conductive tube section 844A can be disposed a first radius (r1), and the third conductive tube section 844C can be disposed at a second radius (r2), different from the first radius (r1). These and other combinations of conductive tube sections 844 that vary in number, wall thickness, radius (r) from the central axis 550, arc distance about the central axis 550, combinations thereof, or the like, are contemplated to fall within the scope of the present invention.

In an embodiment, the one or more conductive tube section(s) 844 can extend through the insulating layer 210, the cladding 600, or both, i.e. a portion of the conductive tube section 844 can extend through the cladding 600 and a portion of the conductive tube section 844 can extend through the insulating layer 210. In an embodiment, one or more layers of insulator layer 210 can extend between the one or more conductive tube section(s) 844.

In an embodiment, the conductive tube section 844 can be formed of a conductive material such as a conductive plastic, conductive polymer, conductive epoxy, metal, alloy, or the like. In an embodiment, the conductive tube section 844 can be formed as a solid-walled structure. In an embodiment, the conductive tube section 844 can be formed of one or more strands of woven or non-woven conductive material.

In an embodiment, each conductive element 230 (e.g. wire 644, conductive tube 744, or conductive tube section 844) can be dedicated to one or more functions of electro-physiological signals from one or more sensors such as one or more of temperature, pressure, oxygen saturation, optical sensor signals, impedance signals, conductance signals, or the like. Alternatively, or in addition to, each conductive element 230 can be configured to transmit electrical energy therealong such as electro-stimulation signals, ablation energy, or the like. Advantageously, the multi-core fiber optic cable 135 including the one or more conductive elements 230 can provide a plurality of functions to the stylet 290.

Advantageously, the conductive tube 744 or conductive tube section 844 can provide an increased cross-sectional area, to provide a reduced electrical resistance to the conductive element 144, while maintaining a reduced overall profile or cross-sectional area to the optical fiber 135. This can provide increased electrical conductance for transmitting increased numbers or types of signals (e.g. electrophysiological signals), or increased electrical energy transmittance required for electrical stimulation or ablation, etc. Further, the optical fiber 135 can include one or more conductive tubes 744 and/or conductive tube sections 844, or combinations thereof. For example, one or more conductive tube sections 844 at a second radius (r2) can provide one or more electrical pathways for one or more electrophysiological signals, while a conductive tube 744 at a first radius (r1) can provide an increase cross-sectional area for increased electrical energy for electrostimulation, ablation, etc. This and other configurations of one or more conductive tubes 744 or conductive tube sections 844 are contemplated to fall within the scope of the present invention.

Figure 11B:
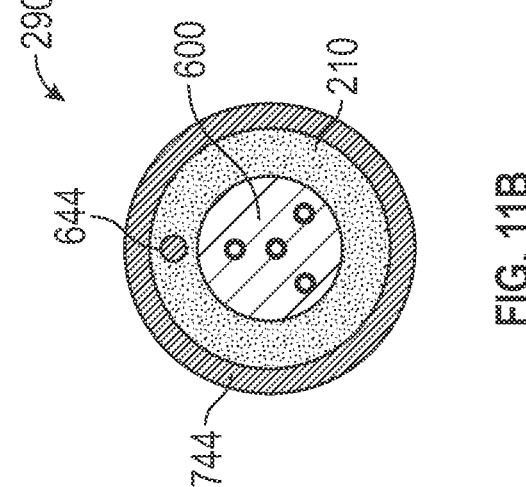
FIG. 11B shows a cross-section view of the multimodal stylet of FIG. 11A, in accordance with embodiments disclosed herein.
Figure 11A:
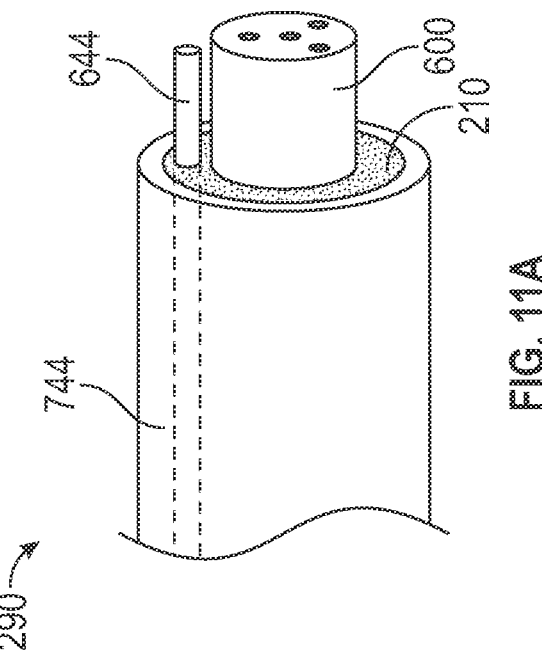
FIG. 11A shows a perspective view of a multimodal stylet including conducting elements arranged linearly and concentrically, in accordance with embodiments disclosed herein.

In an embodiment, as shown in FIGS. 11A-11B, the one or more conductive tube 744 or conductive tube sections 844 can be disposed on an outer surface of the optical fiber 135 and can include one or more insulating layer(s) 210 disposed between the conductive tube 744 or conductive tube section 844 and the central axis 550. In an embodiment, one or more conductive wires 644 can be disposed on an outer surface of the optical fiber 135 and can include one or more insulating layer(s) 210 disposed between the conductive wire 644 and the central axis 550.

In an embodiment, the optical fiber 135 can include a combination of one or more wire conductive elements 644, tubular conductive elements 744, and/or conductive tube sections 844, extending through one or both of the insulating layer 210 and the cladding 600 in either a linear or spiral arrangement, as described herein. Advantageously, the different combinations of conductive elements 230 can be configured to provide different functions of electrophysiology, electrostimulation, ablation, signals, or the like, as described herein.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A fiber-optically enabled medical system, comprising:
an elongate medical device extending longitudinally and formed of a first flexible material, comprising:
an optical fiber having one or more core fibers extending through a cladding layer;
a first conductive element extending parallel to a central longitudinal axis and configured to conduct a first electrical signal for determining a location of a distal tip of the elongate medical device by one or both of a tip location/navigation system (TLS) modality and an ECG modality;
a second conductive element extending parallel to the central longitudinal axis and configured to conduct a second electrical signal, different from the first electrical signal, the second electrical signal including one of an electrophysiological signal or an electro-stimulation signal; and
an insulating layer formed of a second flexible material and disposed between the first conductive element and the second conductive element.

2. The fiber-optically enabled medical system according to claim 1, wherein the first conductive element is a first tube extending annularly about the central longitudinal axis and the second conductive element is a second tube extending annularly about the central longitudinal axis.

3. The fiber-optically enabled medical system according to claim 2, wherein the first tube is disposed at a first radius from the central longitudinal axis, and the second tube disposed at a second radius from the central longitudinal axis, the second radius being different from the first radius.

4. The fiber-optically enabled medical system according to claim 3, further including a second insulating layer disposed between the first tube and the second tube.

5. The fiber-optically enabled medical system according to claim 1, further including a sensor disposed at the distal tip of the elongate medical device and a console coupled to a proximal end of the elongate medical device, one or both of the first conductive element and the second conductive element providing an electrical pathway between the sensor and the console.

6. The fiber-optically enabled medical system according to claim 5, wherein the sensor is configured to detect one of a temperature, a pressure, a blood pressure, an oxygen saturation, electro-optical signals, electrical impedance signals, or electrical conductance signals.

7. The fiber-optically enabled medical system according to claim 1, wherein one or both of the first conductive element and the second conductive element is configured to transmit one of an electro-stimulation signal energy or an ablation signal energy from a console coupled to a proximal end of the elongate medical device to the distal tip of the elongate medical device.

8. The fiber-optically enabled medical system according to claim 1, wherein the elongate medical device includes one of a stylet, a trocar, a guidewire, or a catheter.

\* \* \* \* \*